United States Patent
Gopinath et al.

(10) Patent No.: US 11,311,200 B1
(45) Date of Patent: Apr. 26, 2022

(54) SYSTEMS AND METHODS TO MEASURE PHYSIOLOGICAL FLOW IN CORONARY ARTERIES

(71) Applicant: LightLab Imaging, Inc., Westford, MA (US)

(72) Inventors: Ajay Gopinath, Bedford, MA (US); Samir Farah, Norwood, MA (US); Johan Svanerudh, Uppsala (SE)

(73) Assignee: LIGHTLAB IMAGING, INC., Westford, MA (US)

( * ) Notice: Subject to any disclaimer, the term of this patent is extended or adjusted under 35 U.S.C. 154(b) by 374 days.

(21) Appl. No.: 16/186,040

(22) Filed: Nov. 9, 2018

Related U.S. Application Data

(63) Continuation-in-part of application No. 14/837,291, filed on Aug. 27, 2015.

(60) Provisional application No. 62/584,100, filed on Nov. 9, 2017, provisional application No. 62/042,448, filed on Aug. 27, 2014.

(51) Int. Cl.
| | |
|---|---|
| *A61B 5/0215* | (2006.01) |
| *A61B 5/02* | (2006.01) |
| *A61B 5/00* | (2006.01) |
| *A61B 5/026* | (2006.01) |

(52) U.S. Cl.
CPC ........ *A61B 5/02154* (2013.01); *A61B 5/0084* (2013.01); *A61B 5/026* (2013.01); *A61B 5/02007* (2013.01); *A61B 5/0066* (2013.01); *A61B 5/7203* (2013.01); *A61B 5/7278* (2013.01)

(58) Field of Classification Search
None
See application file for complete search history.

(56) References Cited

U.S. PATENT DOCUMENTS

| | | |
|---|---|---|
| 5,321,501 A | 6/1994 | Swanson et al. |
| 5,459,570 A | 10/1995 | Swanson et al. |
| 5,465,147 A | 11/1995 | Swanson |
| 5,509,093 A | 4/1996 | Miller et al. |

(Continued)

FOREIGN PATENT DOCUMENTS

| | | |
|---|---|---|
| EP | 1 260 175 A2 | 11/2002 |
| JP | 2004-538035 A | 12/2004 |

(Continued)

OTHER PUBLICATIONS

Jeremias et al., "Multicenter Core laboratory Comparison of the Instantaneous Wave-Free Ratio and Resting Pd/Pa with Fractional Flow Reserve The RESOLVE Study", Journal of the American College of Cardiology, 63:13, pp. 1253-1261 (Apr. 8, 2014).

(Continued)

*Primary Examiner* — Yi-Shan Yang
(74) *Attorney, Agent, or Firm* — Foley & Lardner LLP

(57) ABSTRACT

In part, the disclosure relates to computer-based methods, and systems suitable for evaluating a subject to determine the appropriate diagnostic tools for assessing coronary arteries. This can include assessing various blood pressure values during a resting state (without inducing hyperemia). These systems and methods can assess a patient and identify coronary dominance on per patient basis. In turn, this assessment can be used to recommend whether a resting index is appropriate or if another index such as FFR or others such be obtained diagnostic metric such as a pressure value-based ratio.

12 Claims, 13 Drawing Sheets

(56) References Cited

U.S. PATENT DOCUMENTS

| | | |
|---|---|---|
| 5,619,368 A | 4/1997 | Swanson |
| 5,748,598 A | 5/1998 | Swanson et al. |
| 5,784,352 A | 7/1998 | Swanson et al. |
| 5,965,355 A | 9/1999 | Swanson et al. |
| 6,111,645 A | 8/2000 | Tearney et al. |
| 6,134,003 A | 10/2000 | Tearney et al. |
| 6,160,826 A | 12/2000 | Swanson et al. |
| 6,191,862 B1 | 2/2001 | Swanson et al. |
| 6,282,011 B1 | 8/2001 | Tearney et al. |
| 6,421,164 B2 | 7/2002 | Tearney et al. |
| 6,445,939 B1 | 9/2002 | Swanson et al. |
| 6,485,413 B1 | 11/2002 | Boppart et al. |
| 6,501,551 B1 | 12/2002 | Tearney et al. |
| 6,552,796 B2 | 4/2003 | Magnin et al. |
| 6,564,087 B1 | 5/2003 | Pitris et al. |
| 6,570,659 B2 | 5/2003 | Schmitt |
| 6,706,004 B2 | 3/2004 | Tearney et al. |
| 6,865,419 B2 | 3/2005 | Mulligan et al. |
| 6,879,851 B2 | 4/2005 | McNamara et al. |
| 6,891,984 B2 | 5/2005 | Petersen et al. |
| 7,208,333 B2 | 4/2007 | Flanders et al. |
| 7,231,243 B2 | 6/2007 | Fearney et al. |
| 7,241,286 B2 | 7/2007 | Atlas |
| 7,324,848 B1 | 1/2008 | Turcott |
| 7,414,779 B2 | 8/2008 | Huber et al. |
| 7,415,049 B2 | 8/2008 | Flanders et al. |
| 7,625,366 B2 | 12/2009 | Atlas |
| 7,813,609 B2 | 10/2010 | Petersen et al. |
| 7,848,791 B2 | 12/2010 | Schmitt et al. |
| 7,916,387 B2 | 3/2011 | Schmitt et al. |
| 7,935,060 B2 | 5/2011 | Schmitt et al. |
| 8,116,605 B2 | 2/2012 | Petersen et al. |
| 8,206,377 B2 | 6/2012 | Petroff |
| 8,298,156 B2 | 10/2012 | Manstrom et al. |
| 8,325,419 B2 | 12/2012 | Schmitt |
| 8,358,461 B2 | 1/2013 | Huber et al. |
| 8,412,312 B2 | 4/2013 | Judell et al. |
| 8,449,468 B2 | 5/2013 | Petersen et al. |
| 8,478,384 B2 | 7/2013 | Schmitt et al. |
| 8,478,387 B2 | 7/2013 | Xu |
| 8,503,844 B2 | 8/2013 | Petersen et al. |
| 8,581,643 B1 | 11/2013 | Schmitt |
| 8,582,109 B1 | 11/2013 | Schmitt |
| 8,582,619 B2 | 11/2013 | Adler |
| 8,582,934 B2 | 11/2013 | Adler et al. |
| 8,687,201 B2 | 4/2014 | Adler |
| 8,786,336 B1 | 7/2014 | Schmitt |
| 8,831,321 B1 | 9/2014 | Elbasiony |
| 8,948,228 B2 | 2/2015 | Adler |
| 8,953,911 B1 | 2/2015 | Xu et al. |
| 9,152,757 B2 | 10/2015 | Taylor |
| 10,912,463 B2 | 2/2021 | Davies et al. |
| 2002/0072880 A1* | 6/2002 | Svanerudh ........... A61B 5/0215 702/189 |
| 2002/0161351 A1 | 10/2002 | Samson et al. |
| 2005/0201662 A1 | 9/2005 | Petersen et al. |
| 2006/0095065 A1 | 5/2006 | Tanimura et al. |
| 2009/0174931 A1 | 7/2009 | Huber et al. |
| 2009/0306520 A1 | 12/2009 | Schmitt et al. |
| 2010/0076320 A1 | 3/2010 | Petersen et al. |
| 2011/0071404 A1 | 3/2011 | Schmitt et al. |
| 2011/0101207 A1 | 5/2011 | Schmitt |
| 2011/0157686 A1 | 6/2011 | Huber et al. |
| 2011/0190586 A1 | 8/2011 | Kemp |
| 2011/0228280 A1 | 9/2011 | Schmitt et al. |
| 2012/0310081 A1 | 6/2012 | Adler et al. |
| 2012/0238869 A1 | 9/2012 | Schmitt et al. |
| 2012/0250028 A1 | 10/2012 | Schmitt et al. |
| 2013/0010303 A1 | 1/2013 | Petersen et al. |
| 2013/0012811 A1 | 1/2013 | Schmitt et al. |
| 2013/0023761 A1 | 1/2013 | Petroff |
| 2013/0046190 A1 | 2/2013 | Davies |
| 2013/0051728 A1 | 2/2013 | Petroff |
| 2013/0072805 A1 | 3/2013 | Schmitt et al. |
| 2013/0310698 A1 | 11/2013 | Judell et al. |
| 2014/0018669 A1 | 1/2014 | Xu |
| 2014/0024931 A1 | 1/2014 | Winston et al. |
| 2014/0094697 A1 | 4/2014 | Petroff et al. |
| 2014/0114182 A1 | 4/2014 | Petersen et al. |
| 2014/0135633 A1 | 5/2014 | Anderson et al. |
| 2014/0142427 A1 | 5/2014 | Petroff |
| 2014/0142432 A1 | 5/2014 | Hutchins et al. |
| 2014/0142436 A1 | 5/2014 | Hutchins et al. |
| 2014/0181716 A1 | 6/2014 | Merritt et al. |
| 2014/0187929 A1 | 7/2014 | Schmitt et al. |
| 2014/0218742 A1 | 8/2014 | Adler |
| 2014/0249407 A1 | 9/2014 | Adler et al. |
| 2014/0268167 A1 | 9/2014 | Friedman et al. |
| 2014/0276011 A1 | 9/2014 | Schmitt et al. |
| 2014/0276137 A1 | 9/2014 | Bumett et al. |
| 2014/0309536 A1 | 10/2014 | Douk et al. |
| 2014/0379269 A1 | 12/2014 | Schmitt |
| 2015/0025398 A1* | 1/2015 | Davies ................ A61B 5/0215 600/486 |
| 2015/0119705 A1 | 4/2015 | Fochterman et al. |
| 2015/0153157 A1 | 6/2015 | Schmitt et al. |
| 2015/0119707 A1 | 7/2015 | Schmitt |
| 2015/0192405 A1 | 7/2015 | Schmitt |
| 2015/0230713 A1 | 8/2015 | Merritt et al. |
| 2015/0313478 A1* | 11/2015 | Veszelei ................ A61B 5/027 600/483 |
| 2016/0007866 A1 | 1/2016 | Fochterman et al. |
| 2016/0008084 A1 | 1/2016 | Merritt et al. |
| 2016/0058307 A1 | 3/2016 | Svanerudh |
| 2016/0073972 A1 | 3/2016 | Alpert et al. |
| 2016/0135757 A1 | 5/2016 | Anderson et al. |
| 2016/0157785 A1 | 6/2016 | Merritt et al. |

FOREIGN PATENT DOCUMENTS

| | | |
|---|---|---|
| JP | 2012-501807 A | 1/2012 |
| JP | 2014-061268 | 4/2014 |
| JP | 2014-529442 A | 11/2014 |
| WO | 01/13779 | 3/2001 |
| WO | 02/043584 A2 | 6/2002 |
| WO | 2006/041346 | 4/2006 |
| WO | 2012166332 A1 | 12/2012 |
| WO | 2013145638 | 10/2013 |
| WO | 2016/092403 | 6/2016 |

OTHER PUBLICATIONS

International Search Report and Written Opinion for International Application No. PCT/EP2015/069708 mailed from the International Searching Authority dated Dec. 17, 2015 (13 pages).

Mamas et al., "Resting Pd/Pa Measured with Intracoronary Pressure Wire Strongly Predicts Fractional Flow Reserve", Journal of Invasive Cardiology June http://jic.epubxpress.com, 22:6, Jun. 2010, pp. 260-265.

Japanese Office Action and English translation, Application No. 2020-079926, May 18, 2021, 7 pages.

USPTO Office Action, U.S. Appl. No. 14/837,291, dated May 18, 2021, 10 pages.

USPTO Office Action, U.S. Appl. No. 14/837,291, dated Jan. 8, 2021, 23 pages.

USPTO Office Action, U.S. Appl. No. 14/837,291, dated Mar. 27, 2020, 38 pages.

USPTO Office Action, U.S. Appl. No. 14/837,291, dated Sep. 22, 2017, 29 pages.

USPTO Office Action; U.S. Appl. No. 14/837,291, dated Aug. 20, 2021, 13 pages.

Allen et al., "Multicenter Core Laboratory Comparison of the Instantaneous Wave-Free Ratio and Resting Pd/Pa With Fractional Flow Reserve The RESOLVE Study", Journal of the American College of Cardiology, vol. 63, No. 13, Apr. 8, 2014, pp. 1253-1261.

Canadian Office Action, Application No. 2959205, dated Jun. 17, 2021, 5 pages.

Japanese Search Report, Application No. 2020-079926, dated Apr. 21, 2021, and English translation, 50 pages.

(56) References Cited

OTHER PUBLICATIONS

USPTO Notice of Allowance; U.S. Appl. No. 14/837,291, dated Nov. 10, 2021, 10 pages.

* cited by examiner

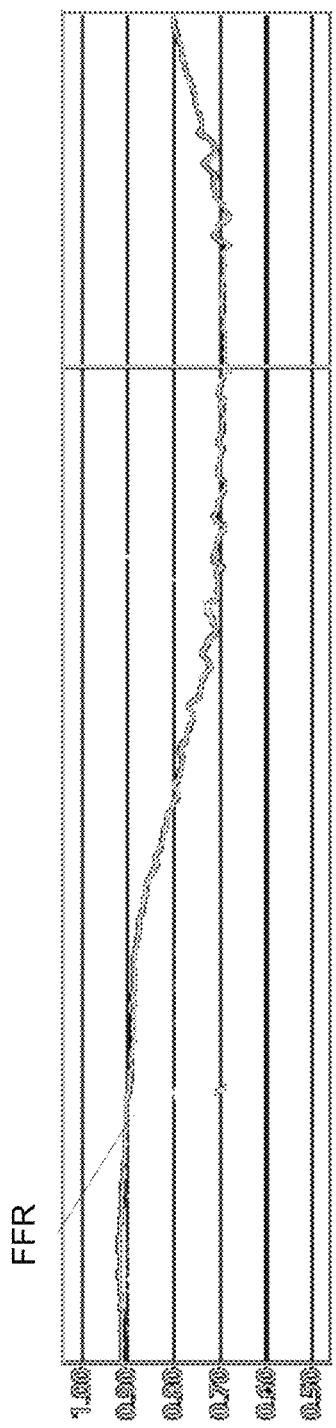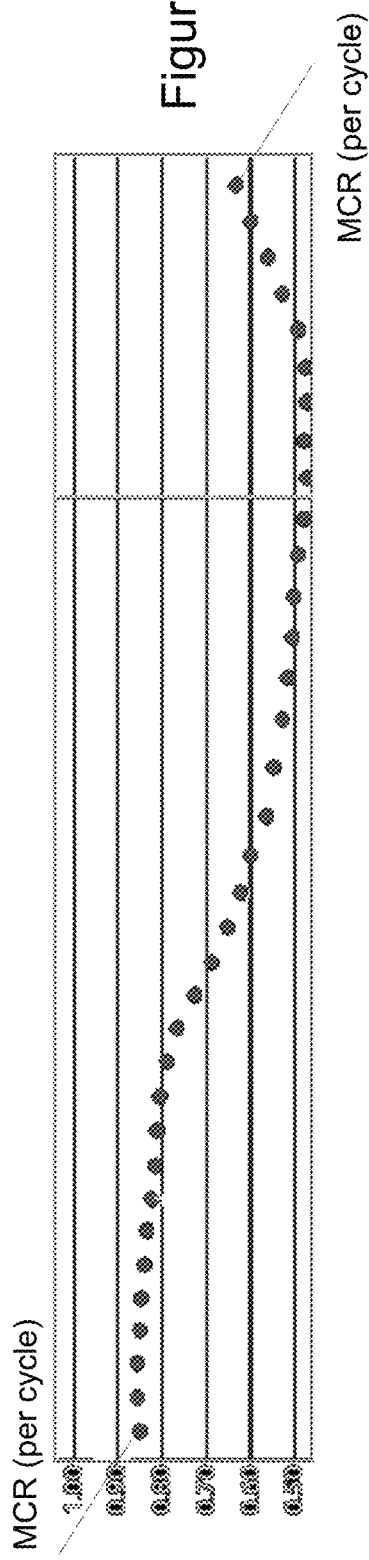

SYSTEMS AND METHODS TO MEASURE PHYSIOLOGICAL FLOW IN CORONARY ARTERIES

CROSS-REFERENCE TO RELATED APPLICATIONS

This application is a continuation-in-part of U.S. patent application Ser. No. 14/837,291, filed Aug. 27, 2015 which claims the benefit of priority under 35 U.S.C. 119(e) from U.S. Provisional Application No. 62/042,448 filed on Aug. 27, 2014 and the benefit of U.S. provisional patent application No. 62/584,100, filed on Nov. 9, 2017, the disclosures of which are herein incorporated by reference in their entirety.

BACKGROUND

Coronary artery disease is one of the leading causes of death worldwide. The ability to better diagnose, monitor, and treat coronary artery diseases can be of life saving importance. Various techniques can be used to obtain intravascular data such via measured parameters or signals suitable for imaging or characterizing an artery. A measurement or sensing device such as a pressure or flow sensor (or other intravascular device) can used to collect data and measured cardiovascular and blood vessel parameters such as length, diameter, and other parameters. Other data collection modalities such as imaging modalities can also be used to help diagnose stenosis and other cardiac system phenomena.

Intravascular optical coherence tomography (OCT) is a catheter-based imaging modality that uses light to peer into coronary artery walls and generate images thereof for study. Utilizing coherent light, interferometry, and micro-optics, OCT can provide video-rate in-vivo tomography within a diseased vessel with micrometer level resolution. This is achieved by pullback an OCT probe through an artery of interest to obtain such details. OCT images provide high-resolution visualization of coronary artery morphology and can be used alone or in combination with other information such as pressure data or other data collecting with a sensing device. Ultrasound based devices such as intravascular ultrasound or IVUS systems and probes can also be used to collect information relating to a subject's cardiovascular system such as by imaging or measuring an artery. OCT, IVUS, and pressure data relating to a subject of interest provide a substantial amount of data about a given cardiovascular system and subsystems and components thereof.

Identifying new diagnostic metrics that advance the field of cardiovascular intervention and others research while avoiding unnecessary complications and assumptions are useful to help simplify and distill the information available to a clinician or other end user of OCT, IVUS, pressure sensing, and other intravascular data collection tools and devices.

The present disclosure addresses these challenges and others.

SUMMARY

In part, the disclosure relates to computer-based methods, and systems suitable for evaluating a cardiac system using a pressure value-based ratio or other diagnostic metrics as described herein. The pressure value-based ratio can be determined using a proximal pressure identified as Pa which can include an aortic pressure and a distal pressure Pd such as a pressure value obtained at a region located downstream from a stenosis. These pressure values can be obtained by sampling two sources of pressure data. Some exemplary sources of pressure data can include a pressure sensor such as an electrical or optical pressure transducer. Suitable pressure sensors can be disposed on, in or otherwise relative to a catheter, such as for example a delivery catheter, an intravascular data collection probe, a guidewire, and other suitable devices and systems. A ratio of Pd/Pa can be determined for each sampled Pd and Pa value of one or more cardiac cycles. A minimum value of each such Pd/Pa ratio can be determined for each cardiac cycle. The set of such minimum values also referred to as MCR values can be plotted over time. The MCR values can be displayed as numerical values or used as inputs to generate other ratios or indices relating to cardiac cycle behavior.

In part, the disclosure relates to a method of tracking cardiac cycle events using intravascular data. The method can include sampling an intravascular data collection probe at a sampling rate to obtain a first plurality of pressure values from a distal region of a vessel; receiving a second plurality of pressure values, at an intravascular data processing system, obtained from a proximal region of the vessel; determining a plurality of distal pressure to proximal pressure (Pd/Pa) ratios from the first plurality of pressure values and the second plurality of pressure values; determining a minimum Pd/Pa ratio from the plurality of Pd/Pa ratios; and displaying the minimum Pd/Pa ratio (MCR).

In one embodiment, the displayed MCR is for a first heart cycle, further comprising determining a plurality of MCRs on a per heart cycle basis. In one embodiment, the method further includes displaying an angiography cine and the plurality of MCRs over time as a pressure wire is pulled back through the vessel. In one embodiment, the method further includes repeating the steps for a plurality of subsequent heart cycles to determine a plurality of MCRs and plotting the plurality of MCRs over time on a per cardiac cycle basis. In one embodiment, the sampling rate ranges from about 25 Hz to about 2 KHz. In one embodiment, the method further includes filtering a waveform generated using a plurality of Pd/Pa ratio values prior to determining one or more minimum Pd/Pa ratios on a per cardiac cycle basis. In one embodiment, the disclosure relates to a diagnostic metric correlated with a patient state of interest that is determined using measurements obtained during a resting condition without hyperemic agents. In one embodiment, the disclosure relates to a diagnostic metric correlated with a patient state of interest that is determined using measurements obtained during a resting condition with a hyperemic agent.

In part, the disclosure relates to a method of analyzing cardiac cycle events in response to a pressure-value based ratio. The method can include receiving a first pressure value measured at a location distal to a region of a blood vessel (Pd1); receiving a first pressure value measured at a location proximal to a region of a blood vessel (Pa1); determining a first ratio of the first pressure value and the second pressure value (R1), wherein R1 corresponds to a first time value; receiving a third pressure value measured at a location distal to a region of a blood vessel (Pd2); receiving a fourth pressure value measured at a location proximal to a region of a blood vessel (Pa2); determining a second ratio of the third pressure value and the fourth pressure value (R2), wherein R2 corresponds to a second time value; and displaying R1 or a plot thereof versus time, if R1 is greater than R2, or displaying R2 or a plot thereof versus time, if R2 is greater than R1. In one embodiment, if R1 is greater than R2, than the first time value corresponds to an occurrence of a pressure reduction in a cardiac cycle. In one embodiment, the pressure reduction is a relative maximum. In one embodiment, the pressure reduction is a maximum for a plurality of cardiac cycles.

In part, the disclosure relates to a system. The system can include an intravascular data collection system comprising an interface to receive data from an intravascular probe; a display system in electrical communication with the intravascular data collection system; one or more memory storage devices comprising instructions to output a user interface on the display system, the user interface comprising one or more regions for displaying a minimum cycle ratio or a plot thereof; a processor in electrical communication with the intravascular data collection system, the display system, and one or more memory storage devices, the processor programmed to sample a plurality of proximal pressure values (Pa) on a per cardiac cycle basis; sample a plurality of distal pressure values (Pd) on a per cardiac cycle basis; determine a set of Pd/Pa ratios for one or more of the sampled Pa and sampled Pd; and identify a minimum ratio value in the set. Some non-limiting examples of intravascular data collection and analysis systems or a component thereof can include a RadiAnalyzer, a RadiAnalyzer Xpress, a Quantien, a PressureWire system (such as *Aeris* 1, *Aeris* 2 or Certus), an Optis system, a multimodal system such as a combination intravascular imaging and pressure monitoring system, a hemodynamic display having a pressure data input. Embodiments of the disclosure can be integrated with the specialized processors and computing devices used in a pressure sensing, OCT, or IVUS system to measure the applicable data and generate the outputs and intermediate steps to determine one or more diagnostic metrics and display them as discrete fixed values or as time varying values.

In part, the disclosure relates to computer-based methods, and systems suitable for evaluating a cardiac system using a diagnostic metric such as a pressure value-based ratio. Selection of a subset or portion of a cardiac cycle is avoided in one embodiment to increase reliability and usability of a diagnostic ratio and parameters described herein. In one embodiment, a minimum or a relative extrema of a series of diagnostic metrics plotted on a per cycle basis are used to inform diagnosis of a stenosis or other intravascular event or phenomena.

In part, the disclosure relates to computer-based methods, and systems suitable for evaluating a subject to determine the appropriate diagnostic tools for assessing one or more coronary arteries of a subject. This can include assessing various blood pressure values during a resting state (without inducing hyperemia). These systems and methods can assess a patient and identify coronary dominance on a per patient basis. In turn, this assessment can be used to recommend whether a resting index is appropriate or if another index such as FFR (non-resting/hyperemia induced) or others should be obtained. Various diagnostic metrics such as a pressure value-based ratio can be used when a resting index is not suitable for a given subject.

In one aspect, the present application relates to a method of determining one or more diagnostic metrics to assess a blood vessel using intravascular data. In one embodiment, the method includes the step of sampling a sensor of an intravascular data collection probe disposed in the blood vessel at a sampling rate to obtain one or more sampled distal pressure values (Pd). The method may include receiving one or more proximal pressure values (Pa) at an intravascular data processing system, and determining, using the intravascular data processing system, a set of (Pd/Pa) ratios from the one or more sampled distal pressure values and the one or more proximal pressure values. The method may include filtering the set of (Pd/Pa) ratio values using a filter having a time constant TC, ranging from about 1% to about 50% of a heart cycle length. The method may further include determining, using the intravascular data processing system, one or more minimum Pd/Pa ratios from the filtered set of (Pd/Pa) ratios, and displaying a representation of at least one minimum Pd/Pa ratio.

In one embodiment, the at least one minimum Pd/Pa ratio used in the method is a minimum relative to one heart cycle, and determined on a per sample basis. In another embodiment, the method further includes selecting the filter such that the repeatability of one or more minimum Pd/Pa ratios increases. In yet another embodiment, the method may further include increasing the repeatability of the one or more minimum Pd/Pa ratios in response to the filtering, such that the filtering reduces signal noise or noise from heart rate fluctuations. In still another embodiment, the method may include averaging the one or more minimum Pd/Pa ratios to obtain the at least one minimum Pd/Pa ratio, where each such ratio is determined on a per heart cycle basis.

In one embodiment, the representation of the at least one minimum Pd/Pa ratio in the method is a representation of a plurality of minimum Pd/Pa ratios, and includes a discrete point for each of the minimum Pd/Pa ratios such that each discrete point corresponds to one heart cycle. In another embodiment, the step of sampling the sensor further includes sampling the sensor during a pullback of the intravascular data collection probe through the blood vessel and displaying minimum Pd/Pa ratios that change along a pullback path in the blood vessel. In yet another embodiment, the method may include displaying a user interface comprising minimum Pd/Pa ratios for a user to evaluate the physiologic significance of a stenosis. In still another embodiment, the method may include monitoring a minimum Pd/Pa value over a time period T and identifying a change in the minimum Pd/Pa value as an indication of a stenosis in the blood vessel. In another embodiment, the one or more proximal pressure values and the one or more distal pressure values are obtained during one or more cardiac cycles that include diastole, systole or a combination thereof.

In one embodiment, the method may further include tracking changes in the minimum Pd/Pa ratios along a pullback path in the blood vessel to identify a location of stenosis in the blood vessel. In one embodiment, the at least one minimum Pd/Pa ratio is a minimum relative to a plurality of heart cycles. In yet another embodiment, the method may include displaying a user interface, where the user interface includes the representation of at least one minimum Pd/Pa ratio. In still another embodiment, the user interface may further include a user interface representation selected from a group consisting of a plot of minimum Pd/Pa values versus a time period, a FFR value, a Pd value, a Pa value, a Pa moving average, a Pd moving average, and an intravascular image.

In another aspect, the present application relates to an intravascular data analysis system to assess a blood vessel. In one embodiment, the intravascular data analysis system may include an interface system to receive intravascular pressure data, a display system, one or more memory storage devices comprising instructions, and a processor in electrical communication with the interface system, the display system, and one or more memory storage devices. In one aspect, the interface system may receive one or more distal pressure values (Pd) measured from an intravascular data collection probe and one or more one or more proximal pressure values (Pa). In another aspect, the processor may be configured to execute instructions to determine a set of (Pd/Pa) ratios from the one or more distal pressure values and the one or more proximal pressure values, filter the set of (Pd/Pa) ratio values using a filter having a time constant TC, wherein the time constant TC ranges from about 1% to about 50% of a heart cycle length, determine one or more minimum (Pd/Pa) ratios from the set of filtered (Pd/Pa) ratios, and display a representation of the at least one minimum (Pd/Pa) ratio.

In one embodiment, the at least one minimum Pd/Pa ratio may be selected from the group consisting of a minimum relative to one heart cycle and a minimum relative to an average of one or more minimum Pd/Pa ratios, where each respective minimum is determined on a per sample basis. In another embodiment, the filter may be selected such that the repeatability of one or more minimum Pd/Pa ratios increases. In yet another embodiment, the processor may be further configured to execute the instructions to increase the repeatability of the one or more minimum Pd/Pa ratios in response to the filtering, such that the filtering reduces signal noise or noise from heart rate fluctuations. In still another embodiment, the processor may be further configured to execute the instructions to average the one or more minimum Pd/Pa ratios to obtain the at least one minimum Pd/Pa ratio, where each such ratio is determined on a per heart cycle basis.

In one embodiment, the representation of the at least one minimum (Pd/Pa) ratio includes a time varying graph of Pd/Pa ratios, which includes an overall minimum Pd/Pa ratio. In another embodiment, the at least one minimum Pd/Pa ratio is selected from the group consisting of a minimum relative to one heart cycle and a minimum relative to an average of one or more minimum Pd/Pa ratios, where each respective minimum is determined on a per sample basis. In yet another embodiment, the filter is selected such that the repeatability of one or more minimum Pd/Pa ratios increases.

In one embodiment, the processor may be further configured to execute the instructions to increase the repeatability of the one or more minimum Pd/Pa ratios in response to the filtering, such that the filtering reduces signal noise or noise from heart rate fluctuations. In another embodiment, the processor may be further configured to execute the instructions to average one or more minimum Pd/Pa ratios to obtain the at least one minimum Pd/Pa ratio, where each such ratio is determined on a per heart cycle basis. In yet another embodiment, the representation of the at least one minimum (Pd/Pa) ratio includes a time varying graph of Pd/Pa ratios, which includes an overall minimum Pd/Pa ratio. In still another embodiment, the representation is of a plurality of minimum Pd/Pa ratios, and includes a discrete point for each of the minimum Pd/Pa ratios, such that each discrete point corresponds to one heart cycle. In another embodiment, the one or more (Pd/Pa) ratios are obtained during a pullback of the intravascular probe through the blood vessel, and the processor may be further configured to execute the instructions to display minimum Pd/Pa ratios that change along a pullback path in the blood vessel.

In one embodiment, the processor may be further configured to execute the instructions to track changes in minimum Pd/Pa ratios along a pullback path in the blood vessel to identify a location of a stenosis in the blood vessel. In another embodiment, the processor may be further configured to execute the instructions to display a user interface comprising minimum Pd/Pa ratios for a user to evaluate the physiologic significance of a stenosis. In yet another embodiment, the processor may be further configured to execute the instructions to monitor a minimum Pd/Pa value over a time period T and identify a change in the minimum Pd/Pa value as an indication of a stenosis in the blood vessel. In still another embodiment, the processor may be further configured to execute the instructions to display a user interface comprising the representation of at least one minimum Pd/Pa ratio and a user interface representation, which is selected from the group consisting of a plot of minimum Pd/Pa values versus a time period, a FFR value, a Pd value, a Pa value, a Pa moving average, a Pd moving average, and an intravascular image.

In part, the disclosure relates to a one or more systems and methods to assess pressure readings relative to the segments of the heart cycle to which they are determined to occur. In one embodiment, the method detects and characterizes the pressure readings based on the occurrence of the readings in the diastolic and systolic regions or segments of the heart cycle. The method may include identifying the dicrotic notch. In some embodiments, the dicrotic notch can be identified by a user viewing a tracing or other presentation of blood pressure values and/or blood pressure ratios. In one embodiment, the dicrotic notch is used to indicate the beginning of the diastolic cycle. Further, with a determination of the location or occurrence of the dicrotic notch in the heart cycle it can be used as a landmark to identify the beginning of the rising pressure values that indicate the end of the diastolic cycle and the beginning of the systolic cycle. In one embodiment, a resting index is determined from the minimum of the filtered ratio of distal and aortic pressure. The temporal occurrence of this minimum or its relative position in the heart cycle is determined. If this minimum occurs in systole, then this patient is identified as having a left dominant circulatory system. In one embodiment, for subjects determined to have a left dominant circulatory/coronary system, the method further provides an assessment that an FFR measurement should be obtained with regard to the subject in lieu of reliance on a resting index.

Although, the invention relates to different aspects and embodiments, it is understood that the different aspects and embodiments disclosed herein can be integrated together as a whole or in part, as appropriate. Thus, each embodiment disclosed herein can be incorporated in each of the aspects to varying degrees as appropriate for a given implementation.

BRIEF DESCRIPTION OF DRAWINGS

The figures are not necessarily to scale, emphasis instead generally being placed upon illustrative principles. The figures are to be considered illustrative in all aspects and are not intended to limit the disclosure, the scope of which is defined only by the claims.

FIGS. 3A-3F are a series of intravascular data sets or plots in accordance with an illustrative embodiment of the disclosure.

DETAILED DESCRIPTION

Various data collection and analysis systems are available to obtain information with regard to the coronary system. The data obtained using a device from a blood vessel or derived data from intravascular or extravascular measurements associated therewith can be analyzed or displayed to provide correlations and extrapolations to assist researchers and clinicians. For example, various measurement systems and intravascular probes are available to determine fractional flow reserve (FFR) with respect to a blood vessel using a pressure-sensor based device. Intravascular ultrasound (IVUS) can also be used in probes to image portions of a blood vessel. In turn, optical coherence tomography (OCT) is an imaging modality that uses an interferometer to obtain distance measurements relative to a blood vessel or objects disposed therein. The systems and devices and resting and non-resting indices can be pair and co-registered with medical imaging systems such as angiography, OCT, and IVUS.

In general, the disclosure can apply to any pressure sensing technology, whether optical, electronic, invasive, non-invasive, image-based, transducer-based, and other systems and devices suitable for obtaining proximal blood pressure values, distal blood pressure values, and other blood pressure values. In general, any suitable pressure sensing device or probe may be used to obtain such values and relay them to the input of the various diagnostic systems described and depicted herein.

Intravascular data collection devices can be used to generate and receive signals that include diagnostic information relative to the blood vessel in which they are used. These devices can include without limitation imaging devices, such as optical or ultrasound probes, pressure sensor devices, and other devices suitable for collecting data with regard to a blood vessel or other components of a cardiovascular system.

Figure 1:
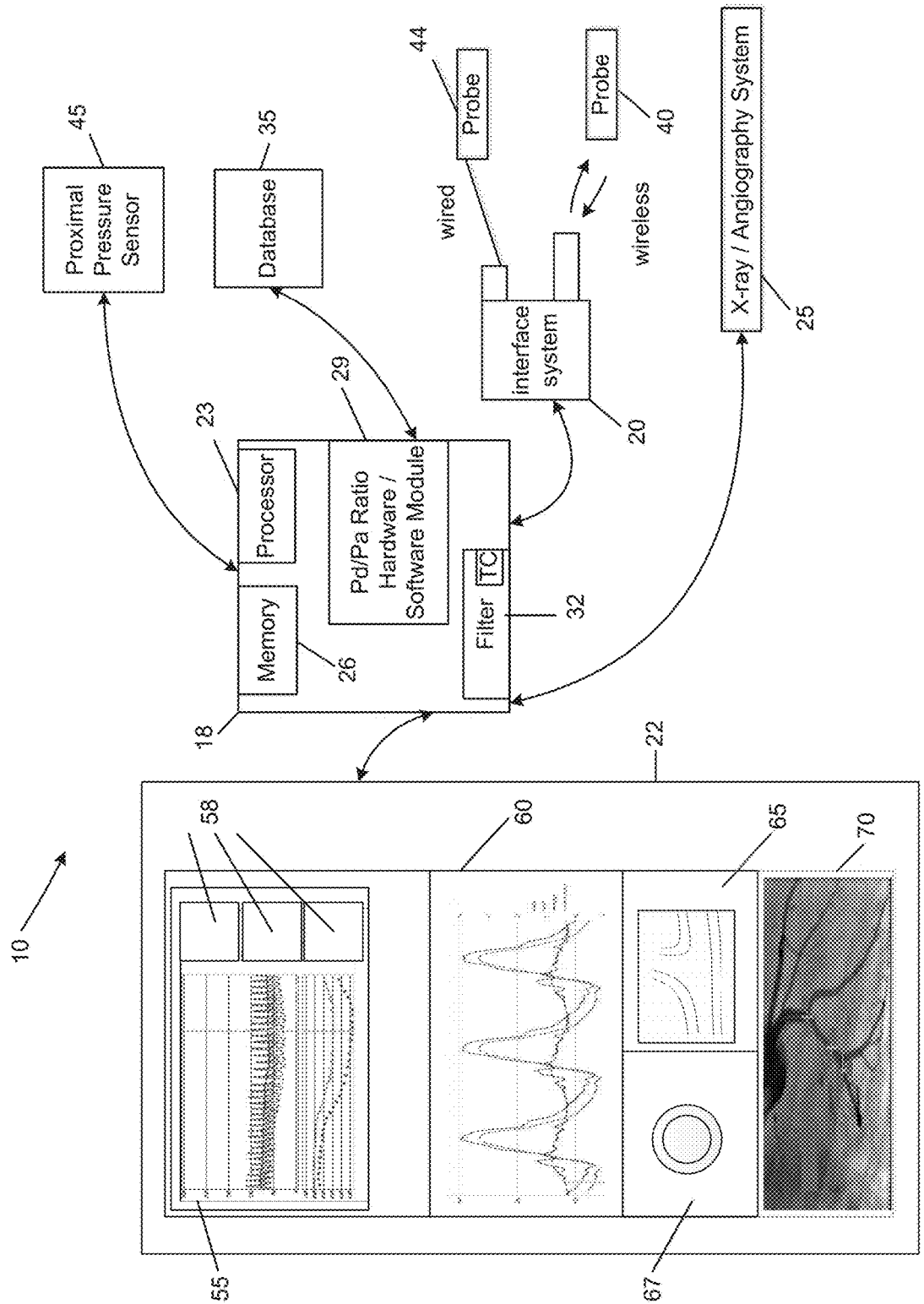
FIG. 1 is a schematic diagram of an intravascular data collection and display system that includes a minimum or threshold-based plot of pressure value ratios in accordance with an illustrative embodiment of the disclosure.

In part, the disclosure relates to intravascular data collections systems and related methods by which intravascular data collected by an intravascular probe can be transformed or analyzed by a processor-based system. The results of such analysis and transformation can be displayed to an end user in various representations such as a display that is in communication with or part of a system such as a pressure monitoring system or intravascular data collection system. Examples of such systems are shown in FIG. 1. In part, using such data to generate one or more indices or ratios correlated with a physiological state of a patient is disclosed.

These ratios or indices are correlated with one or more cardiac system parameters or a patient state such as a stenosis, a treatment regimen, a stent, stent malposition, stenosis severity, stenosis location, infarct size, infarct severity, guiding treatment strategy, evaluating treatment effect, and diagnostic information to assess the need for additional therapy post procedure. The ratios described herein can be determined using pressure values obtained during a resting state of the subject in one embodiment. In another embodiment, the ratios described herein can be determined after the introduction of a hyperemic agent such as adenosine. The use of a hyperemic agent can amplify the associated waveforms in one embodiment.

In one embodiment, a Pd/Pa ratio is continuously calculated using samples of Pd pressure values obtained from one or more pressure sensors or other sampled data used to calculate a pressure value. In one embodiment, pressure data is collected using an intravascular data collection probe disposed in a subject's artery. Exemplary intravascular data collection probes include catheter-based or catheter delivered probes, guidewire based probes, imaging probes, ablation probes, ultrasound probes, interferometry-based probes and other suitable data collection probes and devices. The Pa values are also obtained on a continuous basis from the guide or delivery catheter. The guide or delivery catheter is used to position and advance the intravascular probe through a region of interest in an artery such as a stenosis. The ratio can be calculated on a per sample basis and a one or more Pd/Pa ratios can be determined during each heart cycle. As a result, for a given cardiac cycle a plurality or set of Pd/Pa ratios are obtained.

In the set of Pd/Pa ratios, a minimum Pd/Pa ratio value can be identified. This minimum ratio corresponds to a particular heart cycle and can be identified as a minimum cycle pressure ratio index or as a minimum cycle ratio (MCR). Each MCR for a set of cardiac cycles can be displayed as numerical values or plotted on a display system as described herein. In one embodiment, each MCR is based upon a cardiac cycle rather than a subset or portion thereof. In one embodiment, the MCR is a diagnostic metric that is generated using sampled intravascular data such as a pressure data. The minimum ratios that are obtained when a given subject is in a resting state such that hyperemia has not been induced can be identified as minimum resting Pd/Pa ratios or resting Pd/Pa ratios or resting ratios as applicable.

As an example, if a sample rate of 100 Hz is used to collect Pd and Pa data, for an exemplary one second cardiac cycle, the cycle includes about 100 sample points. These 100 points can be used to determine 100 Pd/Pa ratios. From that set of 100 ratios, a minimum ratio can be identified as the MCR for that cardiac cycle. This process can be repeated for multiple cardiac cycles and plotted over time as shown for example in FIG. 4A. In one embodiment, the sample rate ranges from about 10 Hz to about 100 Hz. In one embodiment, the sample rate ranges from greater than about 25 Hz. In one embodiment, the sample rate ranges from about 100 Hz to about 2000 Hz. In addition, a cardiac cycle can be analyzed using flow curves, EKG, pressure waveforms, and other metrics in conjunction with using MCR values to diagnose one or more states of interest for a subject.

In one embodiment, the methods of determining a ratio as disclosed herein may not be or are not dependent upon ECG triggering or landmark identification. In one embodiment, methods of determining a ratio as disclosed herein may detect a heart rate as an input to adjust a filter parameter such as a sampling period, the time constant or other filter parameter. In one embodiment, ECG triggering or landmark identification is used to determine a heart rate or other input put parameter of the systems and methods. In another embodiment, the maximum pressure reduction in a heart cycle is also identifiable using the methods and systems disclosed herein independent of where such a maximum pressure reduction occurs in a given cardiac cycle. Thus, instead of being determined solely with regard to diastole, the minimum cycle ratio and related methods of the disclosure can identify where and when a maximum pressure reduction occurs in a given cardiac cycle. This identification can be performed whether such a pressure reduction occurs in diastole or systole.

Accordingly, embodiments of the disclosure offer greater flexibility and improved accuracy relative to other approaches because the methods and associated ratios are independent or otherwise insensitive to whether the pressure values used to determine a ratio are measured in the left or right coronary system. Some exemplary graphs of flow details relating to the right and left coronary system are shown in FIG. 5. Compared to indexes using pressure averaging over several heart cycles, the minimum cycle ratio may also be more sensitive to changes that occur when the sensor is pulled back across lesions. Thus, after vessel revascularization has occurred or during a pressure pullback the minimum cycle ratio may be more sensitive to pressure changes when compared to a full cycle Pd/Pa. This sensitivity, which can manifest as smaller pressure drops being displayed as higher amplitude values on a display system, can be useful when tracking MCR values during a pullback to locate a stenosis, evaluate the impact after stenting, assess a side branch, and detect disease or other blood vessel features. The greater sensitivity makes the pressure change easier to detect when, for example, a stenosis is identified based on a change in MCR.

In one embodiment, to improve the consistency of a given minimum cycle ratio MCR value, the ratio can optionally be averaged over a number of heart cycles. In one preferred embodiment, the MCR is not averaged over multiple cardiac cycles, but instead is determined on a per cycle basis. The MCR can be displayed as a number on a screen, as a curve, a plot of discrete points, and combinations of the foregoing or in other representations that are based upon, correlated with, or derived from the MCR.

In one embodiment, a display system provides a user interface that includes features that allow certain conditions or other parameters to be used when determining a MCR or other ratio. After recording values or activation, the system can be configured to display the lowest ratio in the entire recording or after a pre-select number of heart cycles based on user selections via a user interface. Each MCR values provides a metric to identify on a per heart cycle basis the occurrence of a maximum pressure reduction in a heart cycle, regardless of pressure sensing location and without ECG triggering or landmark identification. An exemplary system and components thereof of for determining MCR values is described with regard to FIG. 1.

FIG. 1 depicts a cath lab system 10 suitable for analyzing cardiac systems. The system 10 can include various systems such as a data collection and analysis system 18, an interface system 20, a display system 22 and an x-ray system 25 such as an angiography system 25. Some non-limiting examples of intravascular data collection and analysis systems 18 or a component thereof can include a RadiAnalyzer, a RadiAnalyzer Xpress, a Quantien, an *Aeris* system, an Optis system, a multimodal system such as a combination intravascular imaging and pressure monitoring system, a hemodynamic display having a pressure data input.

The data collection and analysis system 18 can include a processor 23 such a microprocessor, a memory 26, a filter 32 having an associated time constant TC, and one or more software modules, circuits, or hardware components such as a diagnostic metric generator 29 such as for example a Pd/Pa ratio hardware component or software module 29. The processor can be in electrical communication with a circuit board of a pressure sensing, OCT, IVUS, or other intravascular data collection system. The time constant TC can be updated with or adapted based on a measured parameter or preset value or be user selected. The data collection and analysis system 18 can also review historic data stored in a database 35 from prior intravascular and extravascular data collection sessions. The results of determining one or more ratios, curves, or other values as described herein can also be stored in database 35. One or more databases can be used for various data sets as applicable.

In part, embodiments of the disclosure relate to various features of pressure sensing devices, measurement systems, and software relating thereto suitable for determining ratios based upon signals sampled from an intravascular data collection probe such as probes 40 or 44. A guidewire-based probe 40, 44 with a semiconductor device that includes components that undergo electrical changes in response to pressure changes can be used to perform pressure monitoring. The embodiments described herein support methods of performing the methods, ratio determination and measurements using a guidewire-based probe and associated software and electrical components of a data collection and analysis system 18. A wired probe 44 or a wireless probe 40 can be used to transmit data that is received by an interface system 20, system 18, or system 22. A sensor 45 such as the proximal pressure sensor of a guide or delivery catheter can also receive proximal pressure values (Pa) such as aortic pressure values.

System 18 can perform measurement calculations based on signals sampled from the intravascular probe. Alternatively, system 18 can receive signals encoding results of calculations performed using circuitry or processing elements disposed in the probe such as for example in the probe's proximal connector. System 18 can also include software, control systems, and data analysis and display devices and processors suitable for graphing and displaying pressure values, FFR values, MCR values, sampled Pa values, sampled Pd values, moving averages and other values relating to the foregoing.

The interface system 20 is connected to one or more circuits or signal processing or control elements. These circuits, elements, and other components of a given intravascular measurement system are used to convert the time varying electrical signals from the guidewire-based probe by sampling a probe 40, 44 or sensor to generate Pd and Pa values which can be received by one or more systems of FIG. 1. The time varying electrical signals can be currents, voltages, resistance changes, or other data correlated with MCR values. The interfaces and displays are formatted and programmed to display these values and others ratios and parameters as described herein using the display system 22.

The display system 22 can include panels, user interfaces, and other screens suitable for displaying pressure data, such as Pd and Pa values, or data derived therefrom 55, 58, angiography images 70, IVUS or OCT images 67, 65, and other intravascular images and data. The displays 22 or interfaces 20 can be part of or in electrical communication, such as by wireless communication, with system 18 that receives data from a guidewire-based probe, OCT, FFR, IVUS, or other systems.

The angiography system 25 can be used to generate cine sequences by which a pressure wire can be observed before and after a data collection pullback. In one embodiment, the display system simultaneously displays a cine sequence while displaying MCR values that change in time as a pressure sensor is pullback through a vessel. The changes in the MCR values can be used to determine areas of stenosis along the pullback path in the artery. These stenosis locations can be identified using a cursor or electronic annotation tool to mark candidate regions for stenting on one or more angiography frames of the cine sequence or for further imaging using IVUS, OCT or another imaging or data collection modality.

Figure 2A:
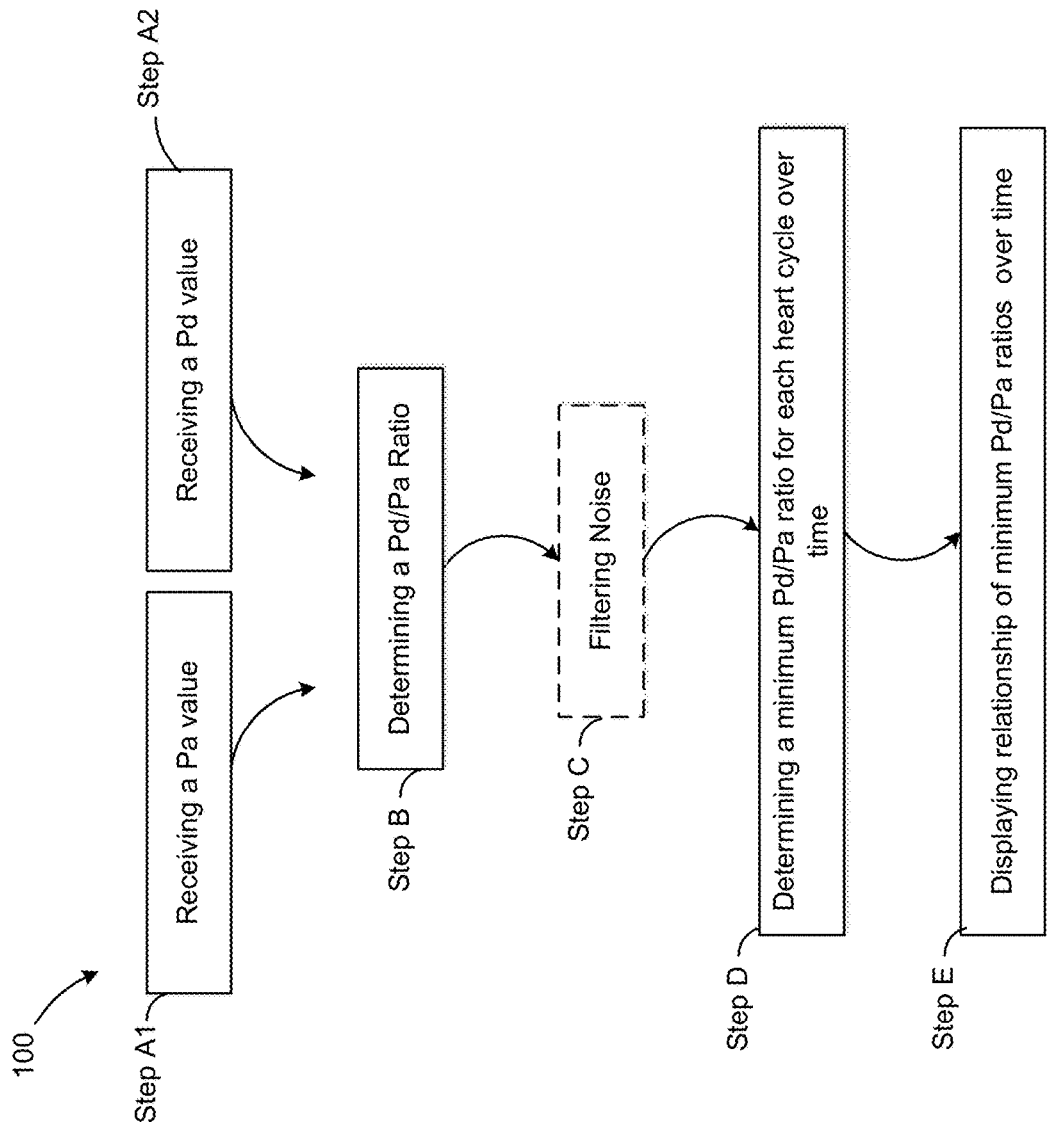
FIG. 2A is a flow chart of an exemplary method of intravascular data analysis and display in accordance with an illustrative embodiment of the disclosure.
Figure 2B:
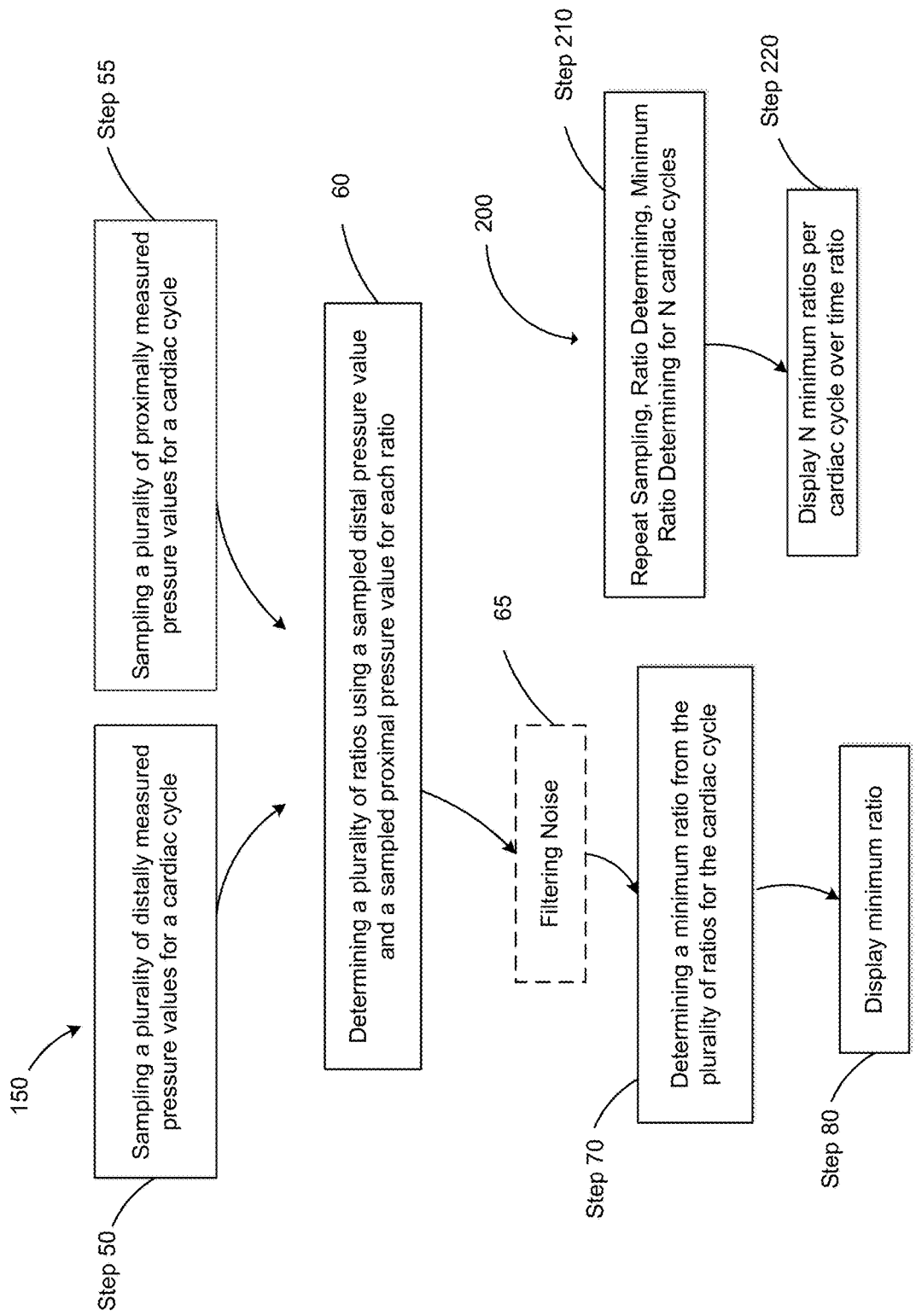
FIG. 2B is a flow chart of an exemplary method of intravascular data analysis and display in accordance with an illustrative embodiment of the disclosure.

The Pa pressure values obtained from a pressure sensor such as mounted on a catheter or guidewire, or otherwise calculated using other measurements, can be used in conjunction with Pd pressure values sampled from a given intravascular probe to determine one or more ratios such as MCR values. These ratios can be displayed or plotted as described herein. FIGS. 2A and 2B show exemplary methods for determining one or more such ratios. Although the ratio are described here as minimum values, the values can also be determined as falling within a particular threshold or other range such as being within a certain percentage of an absolute minimum value or a stand deviation from a minimum value.

Although a minimum value is preferred in certain circumstances, in circumstances where a minimum value is referenced herein a threshold value can also be used that is not a minimum but within range of a minimum value by a predetermined threshold. Thus, a threshold value of between greater than about 0% to less than about 20% of a minimum value such as a Pd/Pa ratio can be used on a per cycle basis in one embodiment. In one embodiment, the Pd/Pa ratio is a diagnostic metric that can be displayed relative to a user interface or display panel of an OCT, IVUS, pressure sensing, flow sensing or other system. The diagnostic metric facilitates decision making relative to a subject for a user such as a clinician.

As shown in FIG. 2A, the method includes the steps of receiving a Pa value and receiving a Pd value. These steps A1 and A2 can be performed separately or together. The values can be received by a component of system 10 such as data collection and analysis system 18. In one embodiment, multiple Pd and Pa values are received over time and are associated with individual cardiac cycles during which they are collected. The method also includes determining a Pd/Pa ratio (Step B) based upon the received Pa and Pd values. In one embodiment, multiple Pd/Pa ratios are determined. An optional filtering step may be part of the method (Step C). Filtering the Pd/Pa ratio traces or curves can be used to smooth such traces or curves by removing noise. The filter can be of various types such as a low pass filter, a high pass filter, a moving average filter, similar filters or combinations thereof, and other suitable filters. The time constant TC for the filter can range from about 10 ms to about 500 ms.

The application of a filter to the ratio curve increases the repeatability of the MCR value for a given cardiac cycle in one embodiment. In one embodiment, the time constant TC will affect the MCR value. This is important for instance when a patient has greatly fluctuating heart rate, bradycardia or tachycardia. The TC constant can be a pre-selected constant in one embodiment having a TC range from about 10 ms to about 500 ms, preferred subset between 100 and 300 ms. In one embodiment, the TC is adaptive and can change over time or have a relationship with one or more parameters such as heart cycle length or another cardiac system or vessel parameter. For example, an adaptive TC can be used that is determined a percentage of the heart cycle length. The heart cycle length can be measured during a data collection session and used as an input to generate the adaptive TC. An adaptive TC can be of the form of TC=a (heart cycle length), wherein a is a percentage. The percentage for such an adaptive TC can range from about 1% to about 50% of a heart cycle length. The methods can include displaying a series of minimum Pd/Pa ratios over a period of time that includes multiple occurrences of systole and diastole. The TC can be adjusted by a user via a user interface, be a fixed valued stored in the data collection system, be updateable via network or firmware updates, or otherwise configured as is suitable for a given scenario.

Still referring to FIG. 2A, given that one or more Pd/Pa ratios have been determined, the method also includes the step of determining a minimum Pd/Pa ratio (MCR) (Step D). A minimum, a relative extrema, or a value correlated or derived from the foregoing can be used as a diagnostic metric in one embodiment. A threshold value such as a percentage of a minimum ratio can also be used for this and other MCR determination embodiments. This determination process can be performed for each heart cycle over time. Once one or more MCR values have been determined these ratios can be displayed as numerical values on a display system or plotted over time such as shown in the figures of the disclosure (Step E). FIG. 2B shows another exemplary embodiment of method 160 of determining and displaying a MCR. Steps 50 and 55 can be performed together or separately. Step 65 is an optional filtering step. Steps 60, 70, and 80 can be performed as shown. The process of FIG. 2B further illustrates that multiple MCRs can be displayed for N cardiac cycles over time as discrete points, values or curves on a display as shown in process flow 200. In the method 200, steps 210 and 220 are performed. Filtering of noise can also be performed as part of method 200.

Thus, the steps include sampling a plurality of distally measured pressure values for a cardiac cycle. Sampling a plurality of proximally measured pressure values for a cardiac cycle is another step. Determining a plurality of ratios using a sampled distal pressure value and a sampled proximal pressure value for each ratio is a step. Optionally, noise filter can be performed. Determining a minimum ratio from the plurality of ratios for the cardiac cycle can be performed. The ratio can then be displayed as a value, a value that changes, or as a plot of values or points. Repeating Sampling, Ratio Determining, Minimum Ratio Determining for N cardiac cycles can be performed iteratively for N cycles wherein is 1 or greater than 1. In one embodiment, the method includes displaying N minimum ratios per cardiac cycle over time ratio.

Figure 3A:
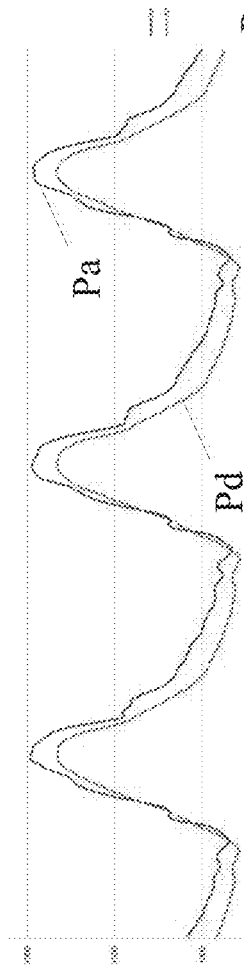
Figure 3B:
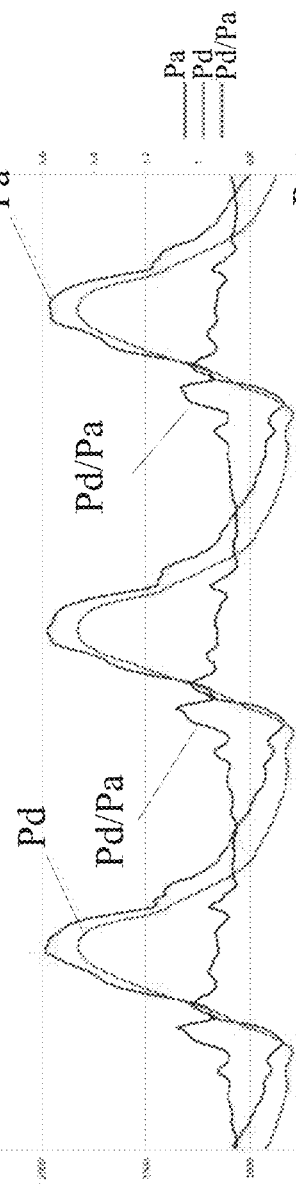
Figure 3C:
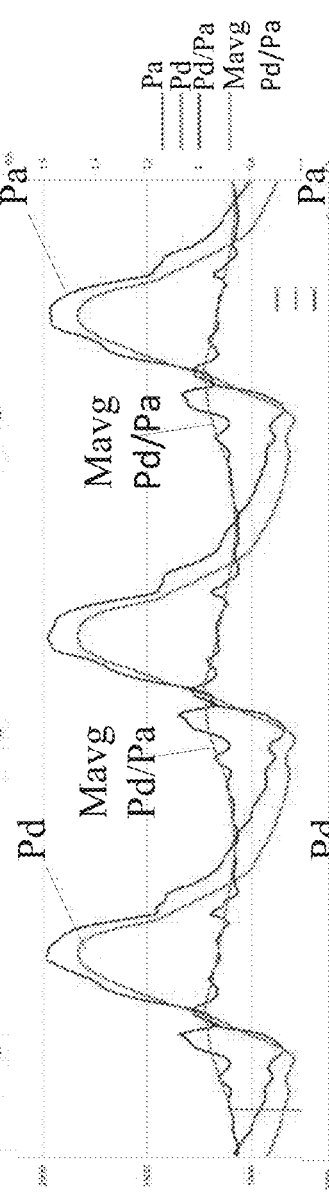
Figure 3D:
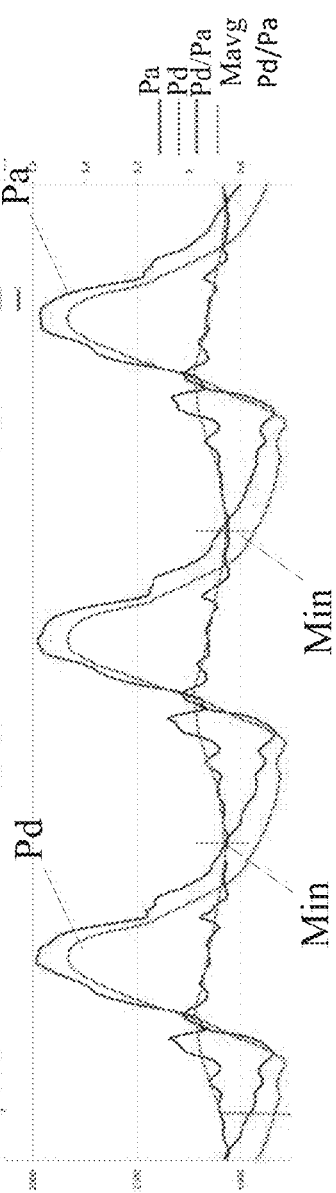
Figure 4A:
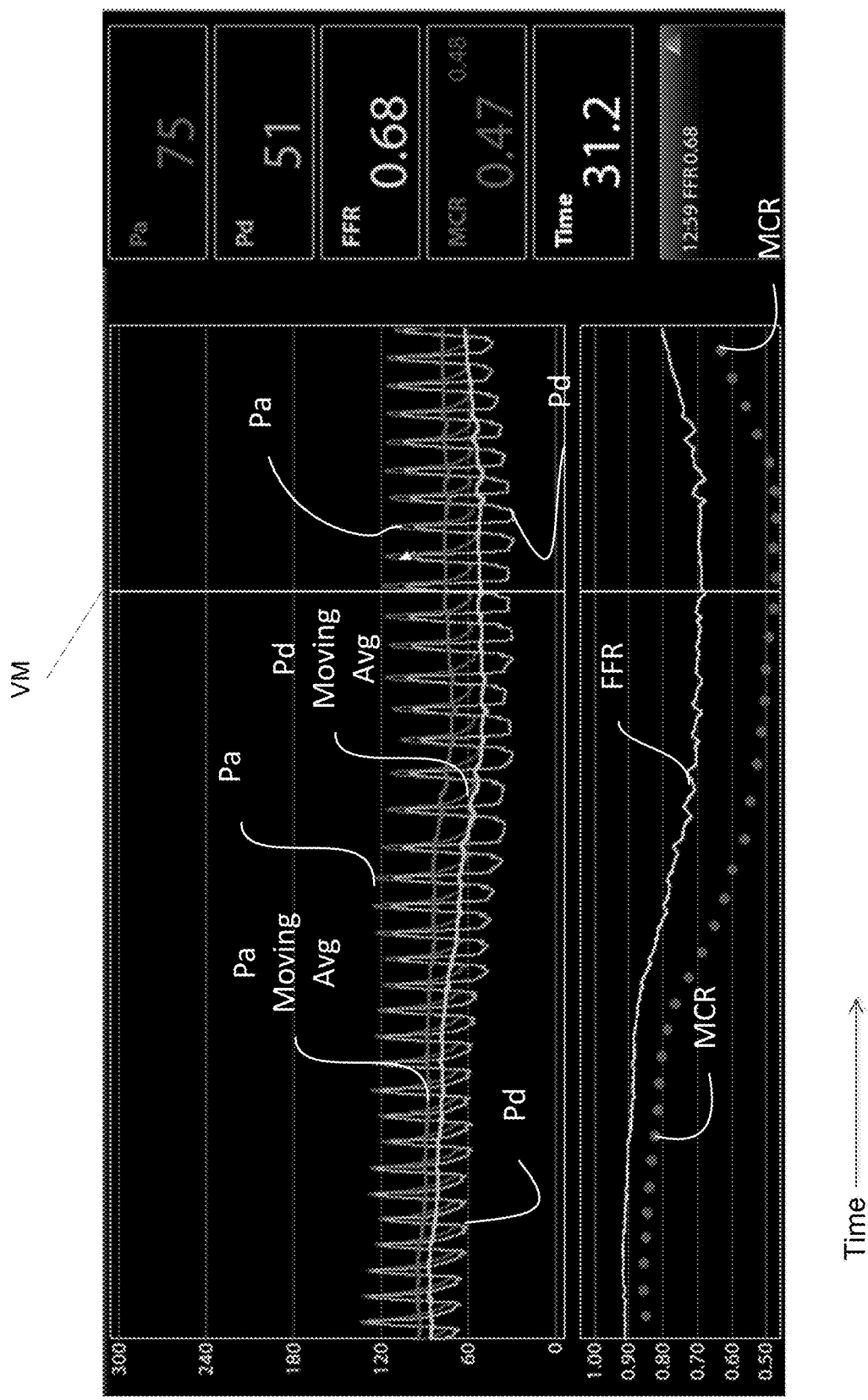
FIGS. 4A and 4B are data displays of intravascular data-based information and relationships over time and on a per heart cycle basis and described herein in accordance with an illustrative embodiment of the disclosure.
Figure 4B:
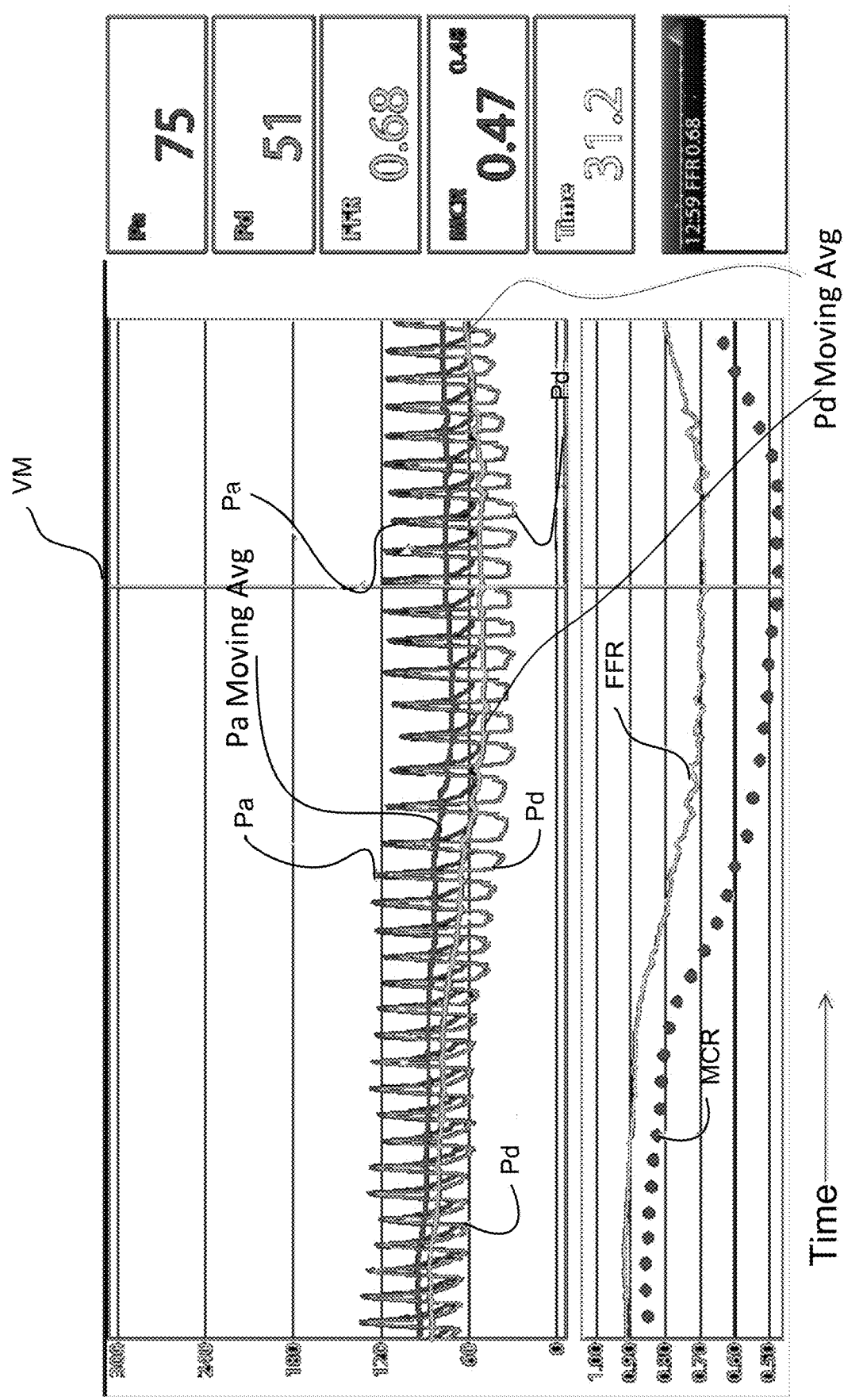

FIG. 3A shows a plot of sampled Pa and Pd values for multiple cardiac cycles. The Pa curve is generally above the Pd curve. FIG. 3B shows the plot of FIG. 3A with the addition of a curve corresponding to the Pd/Pa ratios. In FIG. 3C, the plot of FIG. 3B is shown with the addition of a moving average of the Pd/Pa ratios. In FIG. 3C, the Pd/Pa curve has been smoothed by applying a filter having a time constant TC prior to determining the moving average. The application of such a filter is optional, but can be advantageous under certain scenarios as such as in order to increase repeatability of the MCR measurement regardless of signal noise or fluctuating heart rate. In FIG. 3D, the plot of FIG. 3C is shown with the addition of vertical markers corresponding to the minimum Pd/Pa ratios for two cardiac cycles. These minimum values can be plotted as MCR values over time such as shown in FIG. 3F or 4A and 4B. The images shown in FIG. 3A-3D illustrate the method of generating data using an MCR determination method such as disclosed with respect to FIGS. 2A and 2B. These figures or portions thereof can also be displayed to a user or derivatives thereof to facilitate diagnosis of a subject. Transitions in MCR values can be used in parallel with or in lieu of FFR values to facilitate stent planning.

FIG. 3E shows a plot of FFR values. The FFR values range from about 0.6 to below about 1. The FFR values are plotted versus time with the FFR value be calculated on a per sample basis. The FFR values are determined using the Pd/Pa ratios during hyperemia and averaged over one or several heart cycles over the heart cycles recorded. Measurement of fractional flow reserve (FFR) with a pressure wire is used to as provide guidance for coronary stenting decisions. A distal FFR reading ≥0.8 measured in a coronary branch indicates that Percutaneous Coronary Intervention (PCI) can be safely deferred, because lesions in the branch are not sufficiently narrowed to induce ischemia under hyperemic conditions. Conversely, a distal FFR value <0.8 indicates the need for treatment, usually by implantation of a stent.

FIG. 3F shows a plot of discrete MCR values over time. The MCR values are discrete because they are determined on a per heart cycle basis in the embodiment shown. The MCR values are determined as the minimum Pd/Pa ratio for the sampled Pd and Pa values for a given heart cycle.

FIG. 4A and an alternative graphical representation thereof, FIG. 4B, also show the FFR values of FIG. 3E and the MCR values of FIG. 3F in the bottom panel of the screen. The sampled Pd and Pa values are shown as a tracing in the top panel. In addition, the moving average of the Pa values (Pa Moving Avg) and the Pd values (Pd Moving Avg) are also shown. The Pa Moving Avg is the curve passing through the Pa and Pd peaks. The Pd Moving Avg is the curve disposed below the Pa Moving Avg. In the region of the screen to the right, from top to bottom Pa, Pd, FFR, MCR, and time values are shown corresponding to the position of the vertical marker VM. The vertical marker VM can be programmed to be displayed at a predetermined value or adjustable to cycle through a set of preset positions. The vertical marker VM can also be arbitrarily positioned by the user. As shown, the VM is close to the Pd/Pa minima and MCR minima. In one embodiment, multiple panels of data such as shown in FIGS. 4A and 4B are displayed with a plot or a fixed value or a time varying value of MCR, Pa, Pd, FFR, Time, Pa moving, Pd moving, and averages and weighted combinations of the foregoing. In one embodiment, a display panel with MCR values varying over time is plotted relative to time varying FFR values to facilitate stent planning or other characterization or diagnosis of an artery.

These figures and user interfaces screens can be used with intravascular and angiography images to make stent decisions, identify regions of interest from a diagnostic standpoint, and inform other cardiac system treatment decisions as diagnostic tools. These ratios are also advantageous relative to other approaches for the various implementation and reliability details described herein.

FIGS. 4A and 4B show MCR both at rest and during hyperemia (with the MCR values determined at the same time as FFR). The MCRs determined with the subject at rest may be used to predict the FFR value at hyperemia. Further, MCRs during hyperemia may be used to amplify the stenosis induced pressure difference during hyperemia, as compared to FFR. In one embodiment, a user of the systems, methods, and displays disclosed herein can review a given display of MCR values over time, before a procedure, during a procedure, or after a procedure to diagnoses stenosis severity, stenosis location, guiding treatment strategy, evaluating treatment effect, assessing the need for additional therapy post procedure.

Figure 5A:
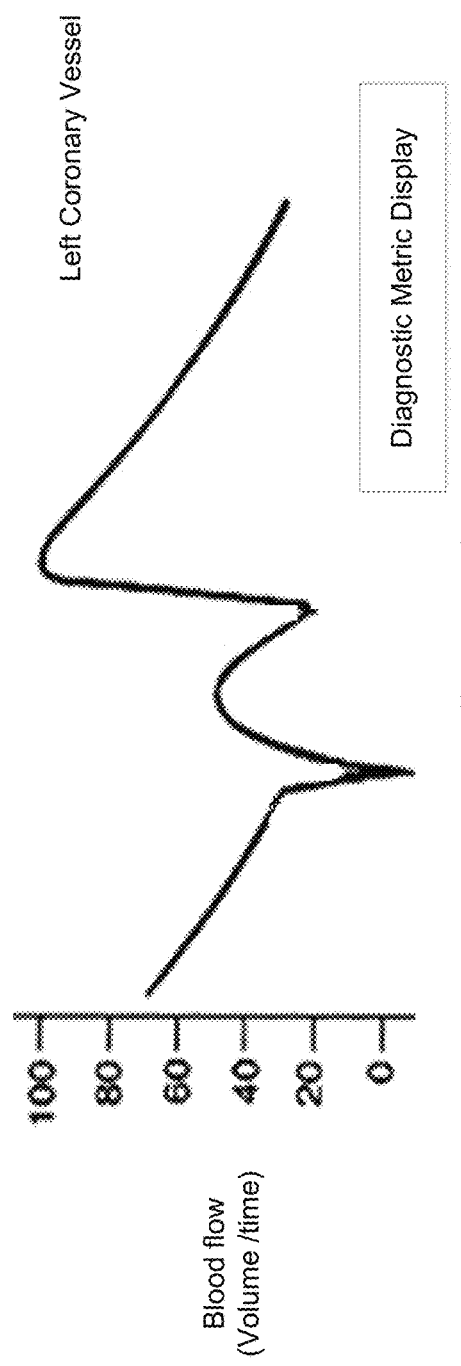
FIGS. 5A and 5B are exemplary plots depicting blood flow patterns in the left and right coronary system and include a diagnostic information display panel or interface in accordance with an illustrative embodiment of the disclosure.
Figure 5B:
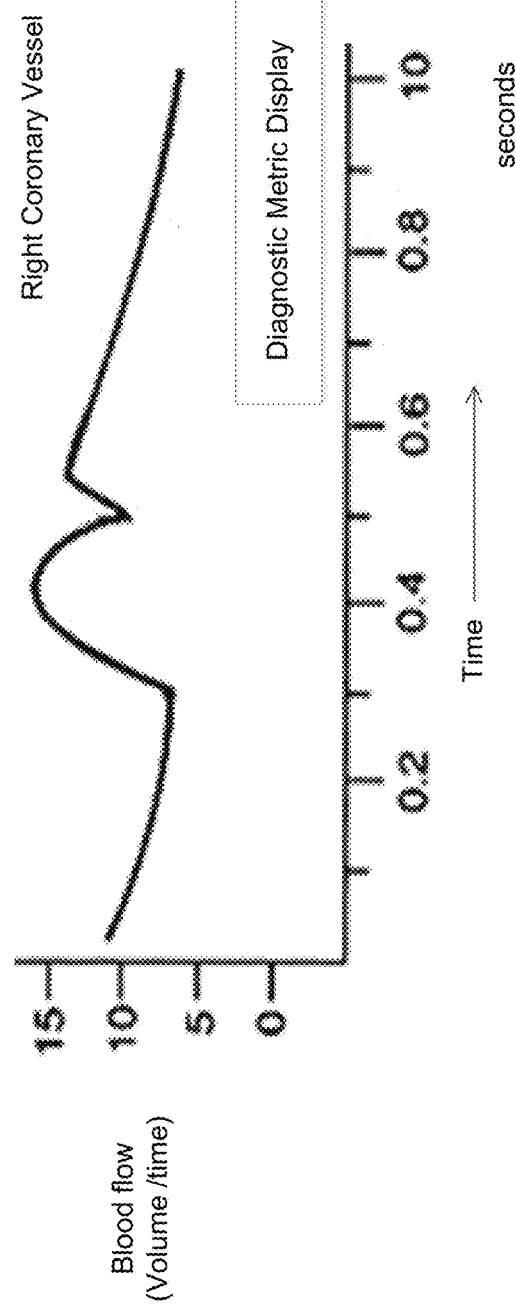

FIGS. 5A and 5B are exemplary plots depicting blood flow patterns in the left and right coronary system. In FIG. 5A, the left coronary vessel's blood flow in terms of blood volume per unit time versus time is shown. In FIG. 5B, the right coronary vessel's blood flow in terms of blood volume per unit time versus time is shown. The ratios and indexes disclosed herein are suitable for describing one or more cardiac cycles and are suitable for use with pressure data collected from either the left or right coronary vessels even though the flow properties of the two vessels differ over time. In one embodiment, the plots of FIGS. 5A and 5B can be displayed as part of a display or user interface of an OCT, IVUS, pressure measurement, flow measurement, or other cardiovascular diagnostic/data collection system as described herein.

In one embodiment, the diagnostic metrics described herein are not specific to a phase of the cardiac cycle such as diastole. The "instantaneous wave free ratio", or iFR, is a method that attempts to correlate an iFR to the more widely used functional index Fractional Flow Reserve, or FFR. In contrast with an embodiment of the disclosure, as part of the process of calculating the instantaneous wave free period, the aortic pressure and coronary artery pressure are averaged during a period of diastole. This iFR methodology is based upon the assumption that the vascular resistance is minimized during diastole and thus would allow lesion assessment in a resting condition without the use of hyperemic agents. The systems and methods described herein provide an assessment of coronary dominance as a result of considering both the systolic and diastolic regions of the heart cycle. This provides a basis to select a hyperemia-based index over a resting index in various instances such as for a subject having a left dominant circulatory system. For example, by assessing systole and diastole, it is possible to determine if the minimum ratio occurs in systole which indicates that the subject being evaluated is identified as having a left dominant circulatory system and a candidate for a FFR or other hyperemic diagnostic assessment as opposed to using a resting index, such as iFR.

There are challenges and uncertainties associated with using an instantaneous wave free ratio. Calculation of a ratio in a specific window in diastole requires precise gating of signals such as by searching for specific values in the pressure waveform. The signal processing and analysis of waveforms adds a degree of complexity in order to use such a ratio and the reliance on diastole may skew the output. Further, as noted above, using the ratio calculated during diastole is based on the assumption that maximum blood flow occurs in diastole. This is not necessarily the case in the right coronary system where flow may be higher in systole, using a diastolic index in the right coronary vasculature may therefore potentially lead to an erroneous assessment of lesion severity. Diastole is a subset of a cardiac cycle. As a result, relying on data collected during a fixed subset of the cardiac cycle may be a source of unreliable results under various circumstances. In one embodiment, the diagnostic methods and associated output metrics described herein are not obtained using such a fixed subset of the cardiac cycle.

Systems and Methods to Measure Physiological Flow Relative to Systolic and Diastolic Segments of Heart Cycle Embodiments In various flow related diagnostic methods, the ratio of a pressure value at a distal location (Pd) and a pressure at a proximal location (Pa) of a coronary artery is determined, such as Pd/Pa. The values of these ratios, including certain minimum values or relative extremum values of the ratio, can be referred to as indices or diagnostics metric. In turn, such indices or metrics may be used to assess ischemia or other events of interest. In general, the reference to a diagnostic index or metric or parameter can be used interchangeably as disclosed herein.

Indices and diagnostic metrics can also be generated using other parameters and models that use such ratios or that are based on other data or computations. With regard to some indices, the underlying pressure values for a ratio-based index such as a Pd/Pa ratio can be obtained from a subject with or without the introduction of an agent that induces hyperemia. Resting indices can generally refer to indices or other diagnostic metrics that are obtained using values obtained from a subject without inducing hyperemia. In one embodiment, a vasodilator or a vasoconstrictor is used to induce hyperemia.

Typically, when determining one or more resting indices, there are certain assumptions that are made. Some of these can negatively affect the results. For example, the value of a given Pd/Pa calculation can be skewed or otherwise be erroneous based on certain design choices inherent to the indices. There are various resting indices computed using only the diastolic region of the pressure curves. In this scenario, where the systolic region of the curve is ignored, any resultant ratios, indices or metrics will fail to provide an accurate diagnostic for patients with a left dominant coronary circulatory system. In this way, resting indices can lead to erroneous results with regard to certain subjects in the overall population.

Accordingly, in part, the disclosure describes systems and methods to tailor the diagnostic metrics and index for a given subject based on one or more subject properties such as, for example, coronary dominance. In addition, using a resting index versus performing an FFR is considered as decision after determining if a subject has a left dominant coronary circulatory system. In one embodiment, data analysis is performed relative to the heart cycle after analyzing the data to locate the dicrotic notch as a landmark. Further, coronary dominance assessment is performed as a step that informs diagnostic index selection for a given subject in an embodiment of the disclosure. In some embodiments, the dicrotic notch can be identified by a user viewing a tracing or other presentation of blood pressure values and/or blood pressure ratios.

In one embodiment, coronary dominance (left dominant, right dominant, and codominant) is determined based upon how blood is supplied to the posterior descending artery. If blood supplied to the PDA from the right coronary artery, the subject is described as right dominant. In turn, if the left coronary artery is supplying blood to the PDA, the subject is described as left dominant. In addition, if the PDA is supplied blood by both the right coronary artery and the left circumflex artery, then the subject is described as codominant.

In part, the disclosure uses pressure data obtained over time from a subject to determine if the subject has a left dominant or right dominant cardio vascular system. With regard to the general population, about 10% to about 15% of subjects are left dominant. With respect to the subpopulation of left dominant subjects, when evaluating Pd/Pa ratios over time for multiple heart cycles, minimum values for the curve have been found to occur in systole. In contrast, with regard to the majority of subjects, the right dominant subpopulation, the minimum values for the Pd/Pa curve have been found to occur in diastole.

These distinctions are important because different diagnostic metrics are suitable for a left dominant subject versus a right dominant subject. If a subject is identified as left dominant, using a resting index in which hyperemia is not induced is not recommended and may lead to erroneous findings. For a left dominant user a full FFR measurement using a hyperemic agent such as adenosine or other vasodilators is recommended in various embodiments. In part, the disclosure describes approaches to assess coronary dominance and recommend diagnostic metrics based upon a determination of left or right or co-dominance. In one embodiment, left dominance defines one diagnostic treatment metric category—hyperemic metric such as FFR. In turn, right dominance and co-dominance are grouped together and define a second treatment category. In other embodiments, right dominance and co-dominance can be assessed as their own separate categories. In part, the disclosure describes approaches to display tracings, data points, or other indicia or representations of a heart cycle that includes both the diastolic and systolic portions of the heart cycle. These portions of the heart cycle can be distinguished based on visual inspection or through automated approached. Automated approaches and visual inspection can distinguish these portions or regions based on their relative position on either side of the dicrotic notch.

In one embodiment, the system describes various steps to determine if a left dominant coronary circulatory system is present for a given subject and, if it is so present, then FFR is recommended as the diagnostic metric for the subject. In contrast, if left dominant coronary circulatory system is not identified, the system recommends a resting index for assessing the subject. In one embodiment, the FFR assessment includes the use of a hyperemic agent.

Figure 6:
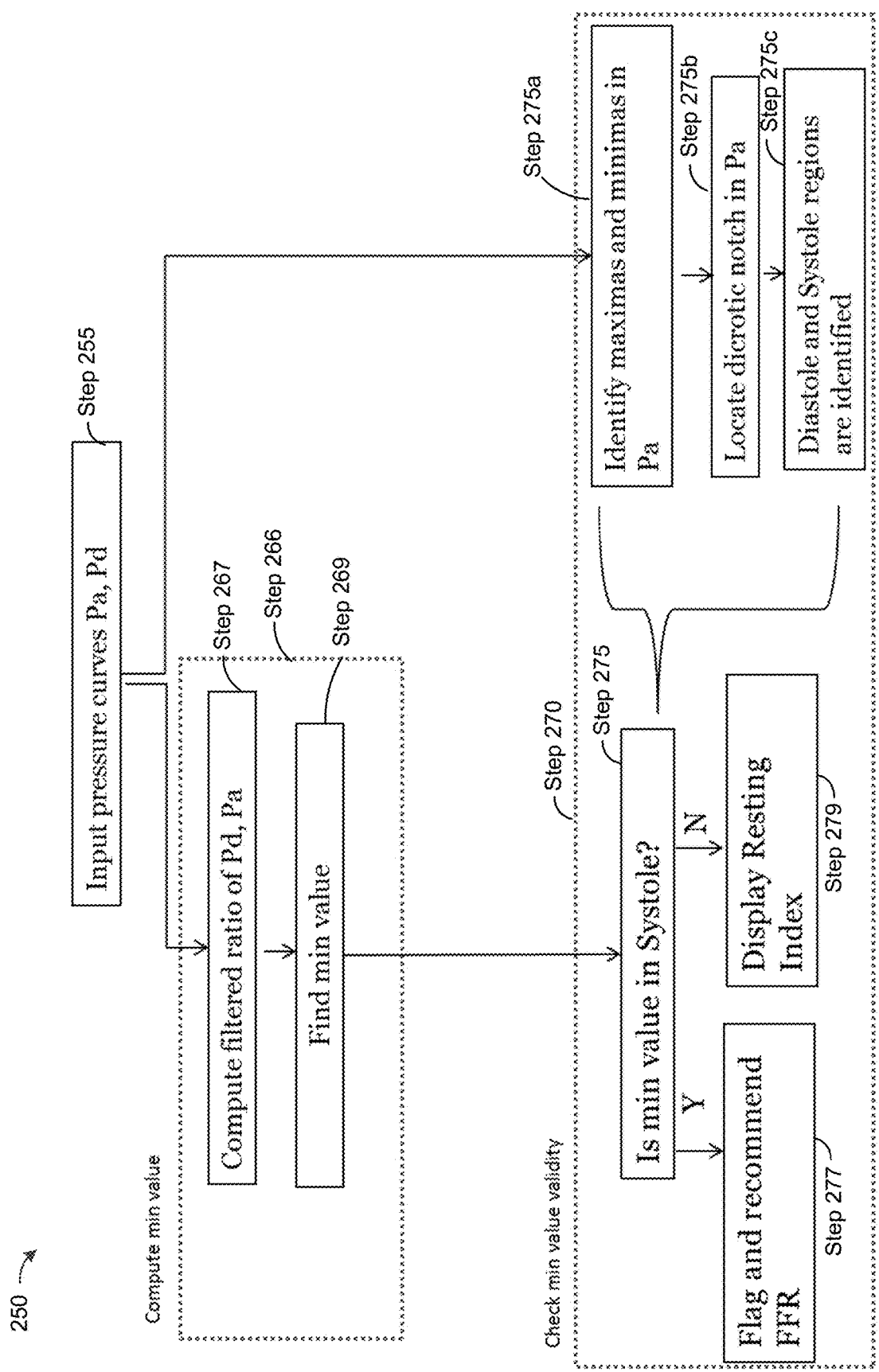
FIG. 6 is flow chart showing various stages and steps to assess pressure data from a subject in order to determine minimum pressure-based index values and determine occurrence of minimum value relative to a portion of the heart cycle in accordance with an illustrative embodiment of the disclosure.

An intravascular data collection system, such as that shown in FIG. 1, can be used to implement one or more steps and processes described herein. The methods described herein can be implemented using some of the steps and methods discussed above. FIG. 6 shows an exemplary method 250 to assess a subject and determine suitability of one or more diagnostic metrics such as FFR or a resting index. The method 250 can include the high level steps of computing minimum values for a given set of subject data Step 266 such as intravascular data discussed above with regard to various figures and methods.

Further, the method 250 can also include the high level step of checking minimum value validity Step 270. That is, is the occurrence of the minimum value component of the index or the index itself valid to use for a given subject as described in Step 270. As part of this process, the method evaluates where/when the minimum occurs relative to the heart cycle Step 275. As shown, this minimum determination step is described in terms of assessing if the minimum occurs in systole Step 275. This assessment can also be done relative to diastole in one embodiment. Steps 275a-275c recite further details relating to determining the location of a given minimum value of an index relative to the heart cycle. It is worth considering the flow of the steps in more detail as describe below.

FIG. 6 is a schematic block diagram of a process flow 250 suitable for assessing coronary dominance and recommending a diagnostic metric. As shown in FIG. 6, the method 250 includes receiving or inputting or otherwise processing Pa and Pd values (Step 255). Initially, pressure data in the form of Pa and Pd values as described herein is input or otherwise received by in electronic memory storage and acted upon by a computing device. In one embodiment, the input data is in the form of input Pa, Pd pressure curves Step 255. The Pa and Pd values can be in the form of curves, vectors, arrays or other data representation and structures.

Filtering is optional in one embodiment and the filtered ratio of Pd and Pa can be determined Step 267 using a computing device of FIG. 1 or as otherwise described herein. At a high level, the process flow determines a minimum value for a Pd/Pa ratio Step 266 as described herein. In one embodiment, a filtered ratio of Pd/Pa is determined Step 267. This can be performed over multiple heart cycles, with each heart cycle including a systolic and a diastolic period. The minimum value for the Pd/Pa ratio can be found for each heart cycle Step 269. In one embodiment, the minimum value is determined for one heart cycle. Typically, the minimum value is determined for multiple heart cycles and thus defines a set of minimum values.

With respect to one or more of the minimum values, the values are assessed to determine if they are valid to use for a given subject Step 270. In one embodiment, whether or not the minimum values are valid for use with the subject they were obtained for is determined based on the location of one or more of the minimum values Step 275. For example, in one embodiment, one or more of the minimum values are assessed to determine if they occur in systole Step 275. In one embodiment, the method includes determining the location of this value relative to segments of the cardiac cycle such as whether the minimum occurs during systole or diastole. With respect to the minimum Pd/Pa values, they are analyzed to determine if they occur in systole Step 275 to determine if a subject has a left dominant coronary system.

Figure 7A:
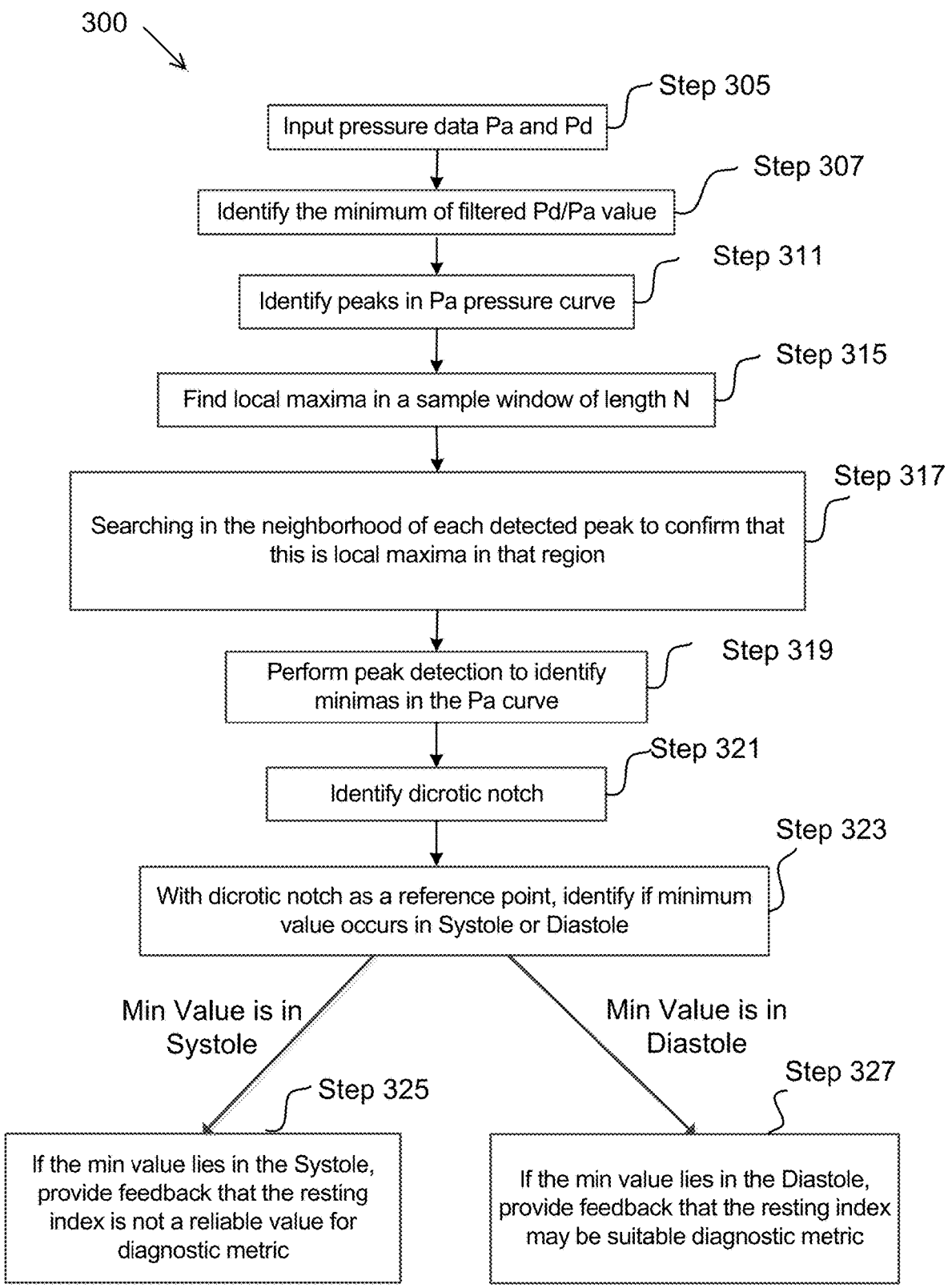
FIG. 7A is flow chart showing various stages and steps to assess pressure data from a subject in order to determine minimum pressure-based index values and determine occurrence of minimum value relative to a portion of the heart cycle in accordance with an illustrative embodiment of the disclosure.
Figure 7B:
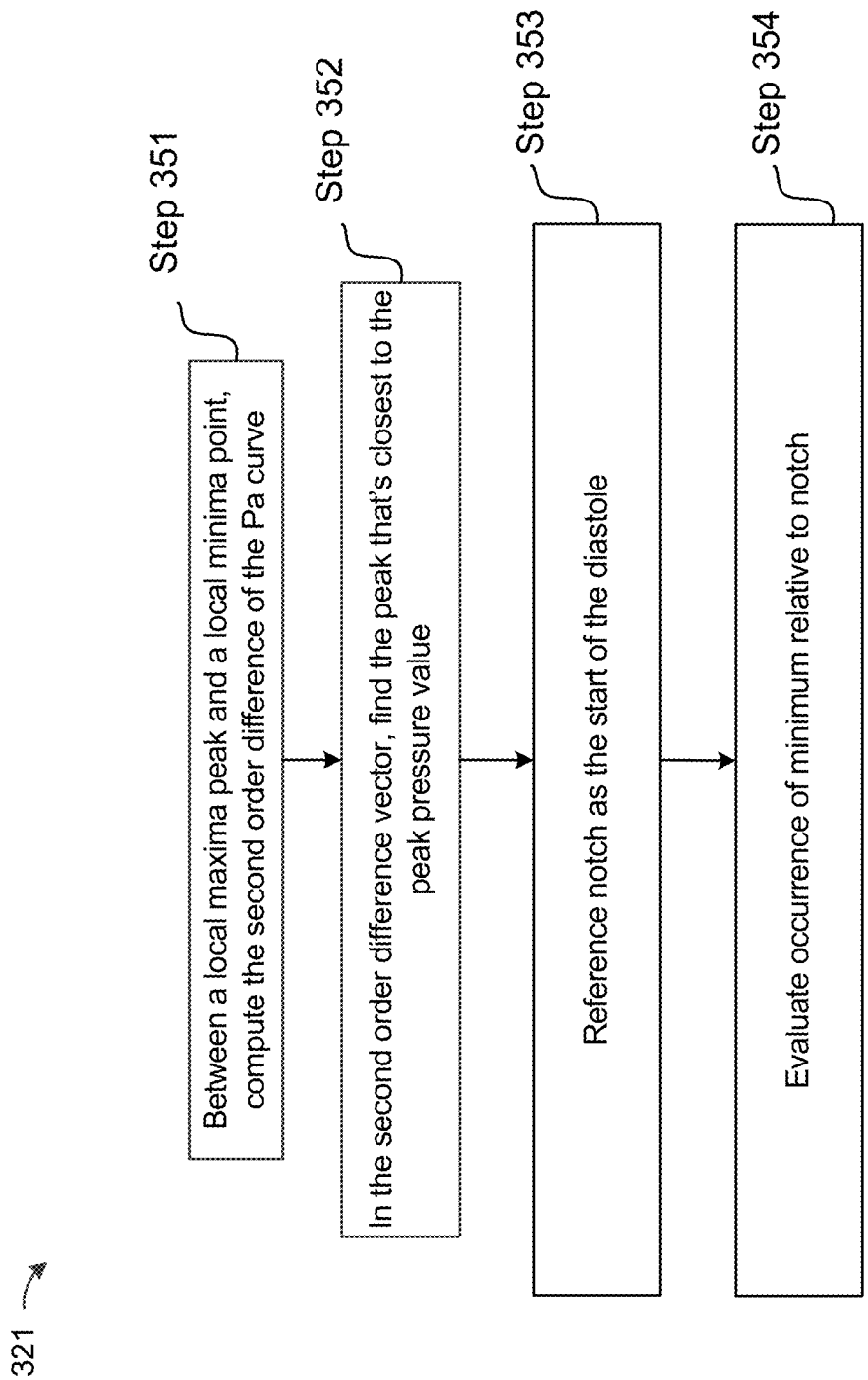
FIG. 7B is flow chart showing various details relating to a method of determining position of dicrotic notch to evaluate occurrence of minimum Pd/Pa ratio for heart cycle in accordance with an illustrative embodiment of the disclosure.

In general, to determine if a given minimum value occurs in systole (per Step 275), various steps can be performed. In one embodiment, the method identifies the maxima and the minima for the Pa values obtained with regard to the subject Step 275a. This set of Pa values is analyzed using various substeps as described herein to locate the dicrotic notch in the Pa data set Step 275b. The dicrotic notch can be located by inspection visually by a clinician. In addition, the dicrotic notch can be located related to the heart cycle or through various time based and pattern matching or tracking methods. The dicrotic notch appears in graphs of aortic pressure (Pa) as small notch or dip. This notch corresponds to the aortic valve closure. Further, the notch is followed by a short uptick corresponding to the dicrotic wave. The dicrotic notch is the start of diastole. The minimum before the pressure curve rises again is the end of diastole. The remaining region is systole. Accordingly, in one embodiment, the dicrotic notch is used to determine where minimum values occur relative to it. In this way, a given minimum value can be assessed as occurring in systole or diastole Step 275c. FIG. 7A provides a further implementation of the process flow to assess coronary dominances and select a diagnostic index. FIG. 7B provides further details relating to an implementation of determining the dicrotic notch.

Returning to FIG. 6, accordingly, after determining a given minimum value occurs in systole, per the inquiry of Step 275, a flag can be generated using the computing device of FIG. 1. If the minimum value occur in systole, the subject is flagged in such a way as to recommend that an FFR be performed using a hyperemic agent Step 277. In general, the system or a user viewing user interface results with minimum in diastole versus systole can provide feedback to a subject under assessment. In one embodiment, the feedback can include indicating a resting index is suitable or an indication that an FFR assessment or another assessment option is worth considering. In contrast, if the minimum value is not systole, or if it is determined as being in diastole, the resting index is displayed as the minimum of the Pd/Pa ration that was obtained using the data and steps described above. In various embodiments, the displayed minimums are shown in one panel of a graphical interface and a tracing or a representation of one or more heart cycles is shown over time. The tracing or representation of one or more heart cycles includes one or more instances of both systole and diastole.

FIG. 7A shows another implementation of a diagnostic method 300 related to the process flow of FIG. 6. The method of FIG. 7A includes the steps of inputting the Pa and Pd pressure data such as in electronic memory storage or by polling or extracting data from a pressure curve Step 305. The method includes identifying the minimum of filtered Pd/Pa value Step 307. Further, the method includes identifying peaks in Pa pressure curve Step 311. The method also includes finding local maxima in a sample window of length L Step 315. In one embodiment, the sample length L is 50. L can be selected as half of the sample rate. Thus, a 100 Hz sample rate yields a window length L of 50.

In one embodiment, the method includes searching in the neighborhood of each detected peak to confirm that this is local maxima in that region Step 317. This can be included as a post-processing step to reduce errors. For example, if a local maximum is just past the window length, it may not be captured. The implementation of a neighborhood search of each detected peak to confirm that this is local maxima in that region addresses this possibility. In addition, the method includes performing peak detection to identify minima in the Pa curve Step 319. With this information, it is useful to identify the dicrotic notch Step 321. With dicrotic notch as a reference point, identify if minimum value occurs in systole or diastole Step 323. If the min value lies in systole, provide feedback that the resting index is not a reliable value for diagnostic metric Step 325. In contrast, if the minimum value lies in diastole, provide feedback that the resting index may be suitable diagnostic metric Step 327. Feedback to the user can be automated or summarized in a user interface or determined by the end user of the system.

Step 321 describes identifying the dicrotic notch. This can be performed in various ways. FIG. 7B shows an exemplary process flow to determine the dicrotic notch as shown by Steps 351 to 354. With the Pa curve data previously input and available in memory of computing device, a difference equation of the Pa curve is determined. In one embodiment, the difference equation compares each data point or vector to the points adjacent to it and generates a difference value. The second order difference equation can also be calculated as the difference equation of the first Pa difference equation. The second order difference equation corresponds to or can be replaced with a second order differential equation. Such an equation facilitates detection of inflection points and other features of the pressure curve.

In one embodiment, determining the dicrotic notch includes between a local maxima peak and a local minima point, computing the second order difference of the Pa curve Step 351. This can be performed by an index-specific software module of the diagnostic system. The output of this step includes a second order difference vector. In the second order difference vector, find the peak that's closest to the peak pressure value Step 351. This peak indicates the location of the dicrotic notch. Reference the dicrotic notch as the start of diastole Step 353. The minimum before the pressure curve rises again are the end of diastole. The remaining region is systole. The system can evaluate occurrence of minimum relative to notch Step 354. If the min value lies in systole, then it is flagged to the user that the resting index is not a reliable value for diagnosis.

Figure 8:
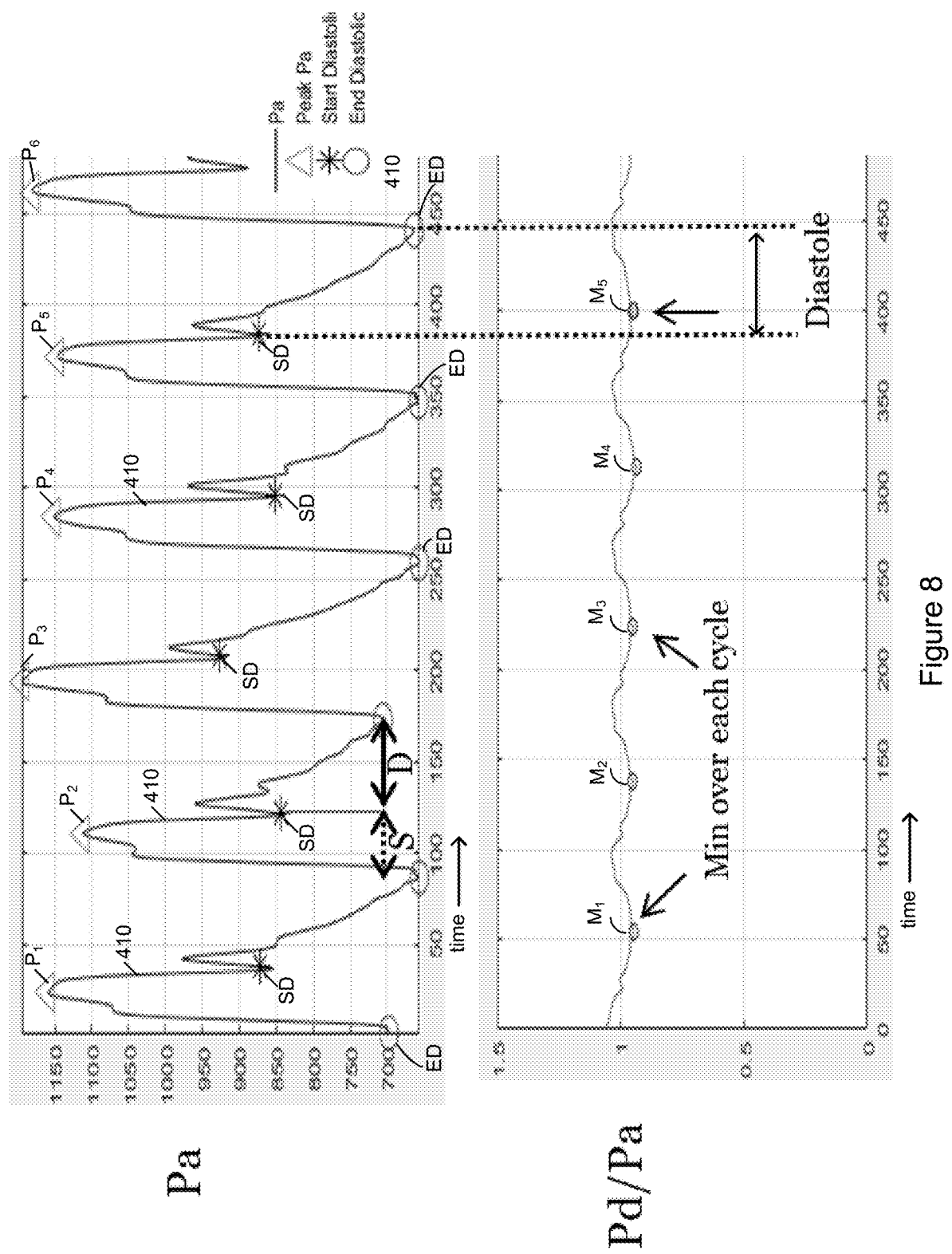
FIG. 8 shows a combination of a Pa pressure curve versus time and Pd/PA curve with minimum values over time in accordance with an illustrative embodiment of the disclosure.
Figure 9A:
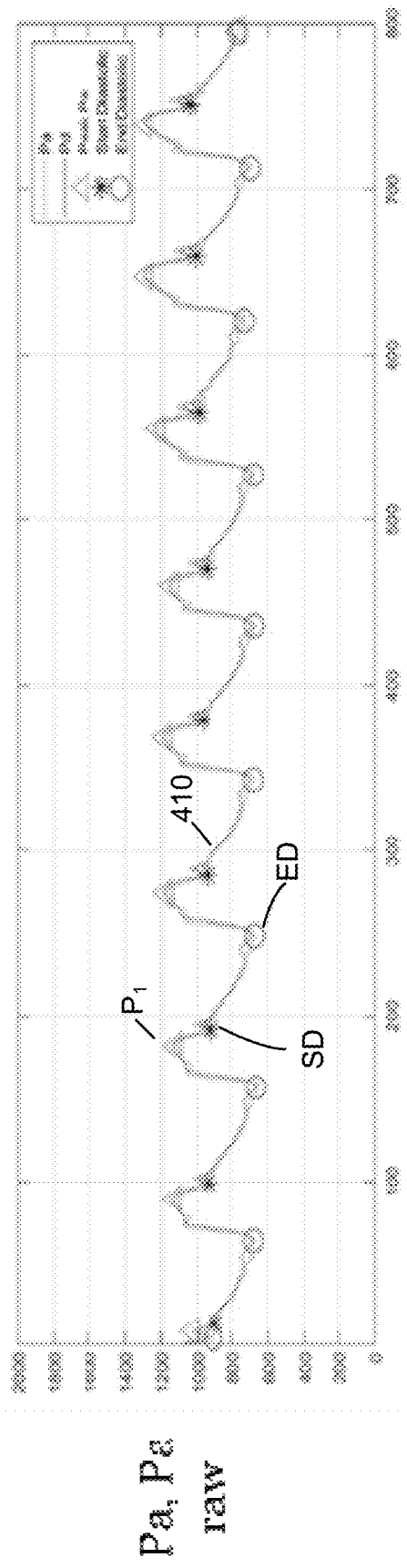
FIG. 9A show a Pa pressure curve versus time that shows diastolic and systolic regions in accordance with an illustrative embodiment of the disclosure.
Figure 9B:
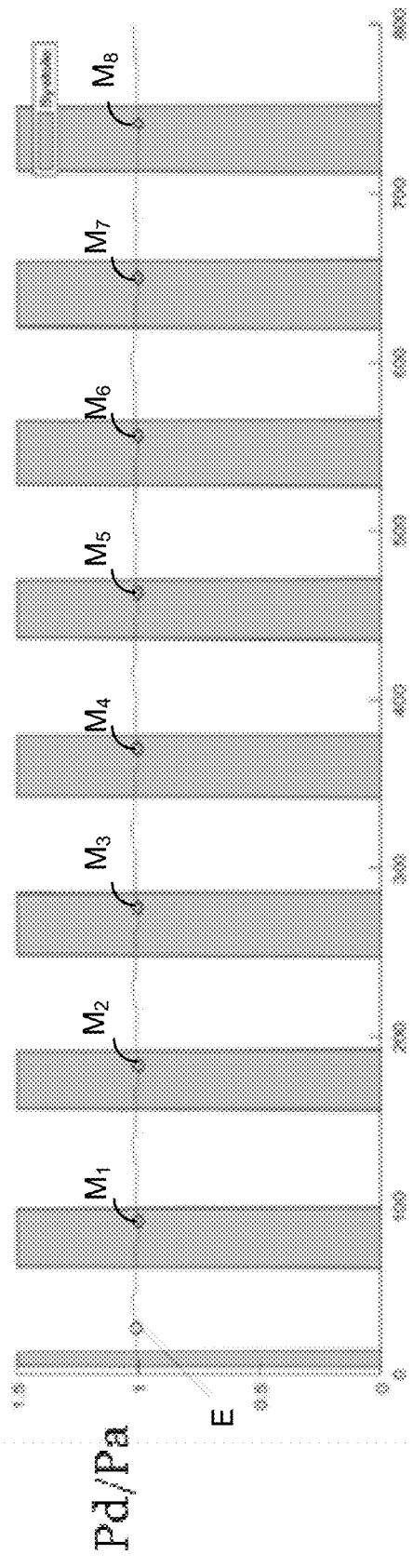
FIG. 9B shows the corresponding Pd/Pa curve for the Pa curve of FIG. 9A in accordance with an illustrative embodiment of the disclosure.

FIG. 8 shows the Pa curve versus time in its upper portion with various peak Pa values P1 to P6. The *'s show the start of diastole (SD) while the O's show the end of diastole (ED). Systole is shown by S and dotted horizontal doubled headed arrow and diastole is shown by D and the solid double headed arrow as one example. In the lower portion of FIG. 8, the Pd/Pa curve is shown with various minimum values M1 to M5 over multiple heart cycles. The heart cycles are shown above in the top portion of the figure. The dotted vertical lines show diastole with minimum value M5 occurring therein. FIG. 8 and FIGS. 9A and 9B relate to different pressure readings for different subjects.

FIG. 9A show a Pa pressure curve versus time. FIG. 9B shows the corresponding Pd/Pa curve for the Pa curve of FIG. 9A. In FIG. 9A, the Pd/Pa curve with the minimum value is indicated with the circle [M1 to M8]. The first min value E is flagged because it was found to fall in systole. M1 to M8 fall in diastole. In one embodiment, the occurrence of a minimum value (Pd/Pa) is tracked to occur in M or more heart cycles. In one embodiment, M is greater than 4. In this way, coughing or other patient effects that can throw off one measurement are avoided by a consistent showing of a minimum Pd/Pa value falling in one part of the heart cycle consistently. Various other features from the curve in FIGS. 8 and 9A and 9B can be used to map minimum values to heart cycle segments.

In general, the disclosure is directed to solving the problem associated with the use of various resting indices. For example, some resting indices are only interested in the diastolic portion of the heart cycle. By ignoring systole, or otherwise failing to consider both portions of the heart cycle—systole and diastole, the applicability of a resting index (no hyperemia) to various patients, can be misplaced. The instant disclosure solves this problem by considering both the systolic and diastolic components of the heart cycle. Additional details on this point are discussed herein.

Measuring a ratio of pressure at the distal to proximal locations of a coronary artery can be used to generate various metrics, indices, and ratios as disclosed herein. In some embodiments, resting indices are used to identify ischemia without inducing hyperemia. However, the resting indices that are computed using only the diastolic region of the pressure curves will fail to provide an accurate answer for patients with left dominant coronary circulatory system. In contrast, various embodiments of the disclosure use systems and methods that will detect and characterize the pressure readings into diastolic and systolic regions or components of the heart cycle.

This division or characterization of the diastolic and systolic regions can be performed by visual inspection of various tracings and pressure readings in a user interface. In some embodiments, the identification of these two regions of the heart cycle is automated using processors or ASICs of a diagnostic system programmed to or running software modules designed to operate on pressure signals and other cath lab parameters. The diagnostic system can identify the dicrotic notch that typically indicates the beginning of the diastolic cycle. The dicrotic notch identifies the beginning of the rising pressure values that indicate the end of the diastolic cycle and the beginning of the systolic cycle. In one embodiment, a resting index is computed as a minimum of a ratio, which may be a filtered ratio, of distal and aortic pressure. The ratio can be obtained as an overall minimum or an average of minimum values or as otherwise described herein.

In one embodiment, if the minimum ratio occurs in systole, then subject being evaluated is identified as having a left dominant circulatory system. For this subject, a recommendation can be generated to obtain additional diagnostic data after inducing hyperemia. Thus, in one embodiment, obtaining FFR assessment, which occurs during hyperemia, is recommended. This recommendation can be automatically generated or can be determined based on reviewing the tracing and resting index values depicted in a graphical interface of a diagnostic system, such as the system of FIG. 1 or other pressure sensing diagnostic systems or probe-based systems, whether non-invasive, invasive, or a combination thereof.

In part, the disclosure relates to a method of assessing a blood vessel during multiple heart cycles. The method includes obtaining, using a pressure sensing device, one or more distal pressure values (Pd) relative to a coronary artery of a subject; receiving one or more proximal pressure values (Pa), at an intravascular data processing system, wherein the one or more Pa values and the one or more Pd values occur during systole and diastole during a non-hyperemic state; determining, using a intravascular data processing system, a set of (Pd/Pa) ratios from the one or more distal pressure values and the one or more proximal pressure values; determining, using the intravascular data processing system, one or more minimum resting Pd/Pa ratios from the set of (Pd/Pa) ratios; and if one or more minimum Pd/Pa ratios occurs in diastole, displaying a representation of at least one resting minimum Pd/Pa ratio.

The method further includes if one or more minimum resting Pd/Pa ratios occurs in systole, performing a fractional flow reserve assessment during hyperemia. The method further includes if one or more minimum resting Pd/Pa ratios occurs in systole, classifying subject as having a left dominant circulatory system and selecting a diagnostic metric based on that classification.

In one embodiment, the method further includes if one or more minimum resting Pd/Pa ratios occurs in systole, inducing hyperemia in the coronary artery. The method further includes sampling a sensor of an intravascular data collection probe disposed in the blood vessel at a sampling rate to obtain one or more sampled distal pressure values (Pd); receiving one or more proximal pressure values (Pa), at an intravascular data processing system; determining, using the intravascular data processing system, a set of (Pd/Pa) ratios from the one or more sampled distal pressure values and the one or more proximal pressure values; filtering the set of (Pd/Pa) ratio values using a filter having a time constant TC, wherein TC ranges from about 1% to about 50% of a heart cycle length; determining, using the intravascular data processing system, one or more minimum Pd/Pa ratios from the filtered set of (Pd/Pa) ratios; and displaying a representation of at least one minimum Pd/Pa ratio.

In one embodiment, the method further includes identifying dicrotic notch in one or more heart cycles or relative to or in a set of Pa values; and determining wherein one or more minimum resting Pd/Pa ratios occurs in diastole or systole based on occurrence of one or more minimum resting Pd/Pa ratios relative to dicrotic notch. In one embodiment, the at least one minimum resting Pd/Pa ratio is a minimum relative to one heart cycle. In one embodiment, the representation includes a time varying graph of resting Pd/Pa ratios, the time varying graph comprising an overall minimum resting Pd/Pa ratio. In one embodiment, the representation is of a plurality of minimum resting Pd/Pa ratios, the representation comprising a discrete point for each of the minimum resting Pd/Pa ratios, each discrete point corresponding to one heart cycle.

In one embodiment, sampling the sensor further includes sampling the sensor during a pullback of the intravascular data collection probe through the blood vessel and further comprising displaying minimum Pd/Pa ratios that change along a pullback path in the blood vessel. The method further includes tracking changes in minimum resting Pd/Pa ratios along a pullback path in the blood vessel to identify a location of stenosis in the blood vessel. The method further includes comprising displaying a user interface comprising minimum resting Pd/Pa ratios for a user to evaluate physiologic significance of a stenosis. The method further includes filtering the set of Pd/Pa ratios by removing noise or by smoothing a waveform comprising the set of Pd/Pa ratios.

In part, the disclosure relates to a method of assessing a blood vessel using intravascular data. The method includes sampling a sensor of an intravascular data collection probe disposed in the blood vessel at a sampling rate to obtain one or more distal pressure values (Pd); receiving one or more proximal pressure values (Pa), at an intravascular data processing system; determining, using the intravascular data processing system, a set of (Pd/Pa) ratios from the one or more distal pressure values and the one or more proximal pressure values; determining, using the intravascular data processing system, one or more minimum Pd/Pa ratios from the set of (Pd/Pa) ratios; identifying dicrotic notch in set of Pa values; determining wherein one or more minimum Pd/Pa ratios occurs in diastole or systole based on occurrence of one or more minimum Pd/Pa relative to dicrotic notch; and if one or more minimum Pd/Pa ratios occur in systole, generate feedback for subject regarding a further assessment option.

In one embodiment, the further assessment option includes an FFR assessment. In one embodiment, the method further includes inducing hyperemia and performing an FFR assessment. In one embodiment, the further assessment option comprises classifying subject as having a left dominant circulatory system and selecting a diagnostic metric based on that classification. In one embodiment, identifying dicrotic notch in set of Pa values is performed by visual inspection. In one embodiment, identifying dicrotic notch in set of Pa values is performed automatically by the intravascular data processing system. In various embodiments, the dicrotic notch is identified in one or more heart cycles. Further, in various embodiments, the dicrotic notch is identified in or relative to a set of Pa values.

The systems and methods disclosed herein can determine, for a resting index and/or a non-resting index (with hyperemia), a minimum relative to one heart cycle and a minimum relative to an average of one or more minimum Pd/Pa ratios, wherein each respective minimum determined on a per sample basis. Further, the systems and methods disclosed herein can use the diagnostic system that receives subject data to average one or more minimum Pd/Pa ratios, for a resting index and/or a non-resting index (with hyperemia), to obtain the at least one minimum Pd/Pa ratio, each such ratio determined on a per heart cycle basis.

Non-Limiting Software Features and Embodiments for Determining Diagnostic Metrics Such as Ratios, Resting Indices, FFR The following description is intended to provide an overview of device hardware and other operating components suitable for performing the methods of the disclosure described herein. This description is not intended to limit the applicable environments or the scope of the disclosure. Similarly, the hardware and other operating components may be suitable as part of the apparatuses described above. The disclosure can be practiced with other system configurations, including personal computers, multiprocessor systems, microprocessor-based or programmable electronic device, network PCs, minicomputers, mainframe computers, and the like. The disclosure can also be practiced in distributed computing environments where tasks are performed by remote processing devices that are linked through a communications network such as in different rooms of a catheter or cath lab.

Some portions of the detailed description are presented in terms of algorithms and symbolic representations of operations on data bits within a computer memory. These algorithmic descriptions and representations can be used by those skilled in the computer and software related fields. In one embodiment, an algorithm is here, and generally, conceived to be a self-consistent sequence of operations leading to a desired result. The operations performed as methods stops or otherwise described herein are those requiring physical manipulations of physical quantities. Usually, though not necessarily, these quantities take the form of electrical or magnetic signals capable of being stored, transferred, combined, transformed, compared, and otherwise manipulated.

Unless specifically stated otherwise as apparent from the following discussion, it is appreciated that throughout the description, discussions utilizing terms such as "processing" or "computing" or "correlating" or "detecting" "assessing" or "measuring" or "calculating" or "comparing" "generating" or "sensing" or "determining" or "displaying," or Boolean logic or other set related operations or the like, refer to the action and processes of a computer system, or electronic device, that manipulates and transforms data represented as physical (electronic) quantities within the computer system's or electronic devices' registers and memories into other data similarly represented as physical quantities within electronic memories or registers or other such information storage, transmission or display devices.

The present disclosure, in some embodiments, also relates to apparatus for performing the operations herein. This apparatus may be specially constructed for the required purposes, or it may comprise a general purpose computer selectively activated or reconfigured by a computer program stored in the computer. Various circuits and components thereof can be used to perform some of the data collection and transformation and processing described herein.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below. In addition, the present disclosure is not described with reference to any particular programming language, and various embodiments may thus be implemented using a variety of programming languages.

Embodiments of the disclosure may be embodied in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other programmable logic device), discrete components, integrated circuitry (e.g., an Application Specific Integrated Circuit (ASIC)), or any other means including any combination thereof. In a typical embodiment of the present disclosure, some or all of the processing of the data collected using an OCT probe and the processor-based system is implemented as a set of computer program instructions that is converted into a computer executable form, stored as such in a computer readable medium, and executed by a microprocessor under the control of an operating system. Thus, query response and input data are transformed into processor understandable instructions suitable for generating ratios based upon sampled pressure values, and otherwise display such ratios and options which change how they are determined for a given pressure data collection session, and other features and embodiments described above.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Various examples of suitable processing modules are discussed below in more detail. As used herein a module refers to software, hardware, or firmware suitable for performing a specific data processing or data transmission task. Typically, in a preferred embodiment a module refers to a software routine, program, or other memory resident application suitable for receiving, transforming, routing and processing instructions, or various types of data such as resistance changes, voltage changes, current changes, guidewire-based probe data, intravascular pressure data, ratios, indices and other information of interest.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the disclosure described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the disclosure.

A storage medium may be non-transitory or include a non-transitory device. Accordingly, a non-transitory storage medium or non-transitory device may include a device that is tangible, meaning that the device has a concrete physical form, although the device may change its physical state. Thus, for example, non-transitory refers to a device remaining tangible despite this change in state.

The aspects, embodiments, features, and examples of the disclosure are to be considered illustrative in all respects and are not intended to limit the disclosure, the scope of which is defined only by the claims. Other embodiments, modifications, and usages will be apparent to those skilled in the art without departing from the spirit and scope of the claimed disclosure.

The use of headings and sections in the application is not meant to limit the disclosure; each section can apply to any aspect, embodiment, or feature of the disclosure.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the disclosure as if each value were specifically enumerated herein. In addition, smaller ranges between and including the upper and lower limits of a given range are contemplated and encompassed within the disclosure. The listing of exemplary values or ranges is not a disclaimer of other values or ranges between and including the upper and lower limits of a given range.

It is to be understood that the figures and descriptions of the disclosure have been simplified to illustrate elements that are relevant for a clear understanding of the disclosure, while eliminating, for purposes of clarity, other elements. Those of ordinary skill in the art will recognize, however, that these and other elements may be desirable. However, because such elements are well known in the art, and because they do not facilitate a better understanding of the disclosure, a discussion of such elements is not provided herein. It should be appreciated that the figures are presented for illustrative purposes and not as construction drawings. Omitted details and modifications or alternative embodiments are within the purview of persons of ordinary skill in the art.

It can be appreciated that, in certain aspects of the disclosure, a single component may be replaced by multiple components, and multiple components may be replaced by a single component, to provide an element or structure or to perform a given function or functions. Except where such substitution would not be operative to practice certain embodiments of the disclosure, such substitution is considered within the scope of the disclosure.

The examples presented herein are intended to illustrate potential and specific implementations of the disclosure. It can be appreciated that the examples are intended primarily for purposes of illustration of the disclosure for those skilled in the art. There may be variations to these diagrams or the operations described herein without departing from the spirit of the disclosure. For instance, in certain cases, method steps or operations may be performed or executed in differing order, or operations may be added, deleted or modified.

What is claimed is:

1. A method of assessing a blood vessel during multiple heart cycles comprising:

sampling a sensor of an intravascular data collection probe disposed in the blood vessel at a sampling rate to obtain a plurality of sampled distal pressure (Pd) values;

receiving, at an intravascular data processing system, the plurality of sampled distal pressure (Pd) values and a plurality of proximal pressure (Pa) values, wherein the plurality of distal pressure (Pd) values and the plurality of proximal pressure (Pa) values occur during a non-hyperemic state;

determining, using the intravascular data processing system, one or more sets of Pd/Pa ratios based on the plurality of distal pressure (Pd) values and the plurality of proximal pressure (Pa) values, wherein each of the one or more sets of Pd/Pa ratios includes Pd/Pa ratios that are determined through an entirety of one heart cycle;

determining, using the intravascular data processing system, one or more minimum resting Pd/Pa ratios, wherein each of the one or more minimum resting Pd/Pa ratios is a minimum among one of the sets of Pd/Pa ratios over the entirety of the corresponding heart cycle;

determining whether the one or more minimum resting Pd/Pa ratios occur in diastole or in systole; and (i) if the one or more minimum resting Pd/Pa ratios occur in systole, inducing hyperemia in the blood vessel, and performing a fractional flow reserve assessment during the hyperemia, or (ii) if the one or more minimum resting Pd/Pa ratios occur in diastole, controlling a display system to generate a plot of the one or more minimum resting Pd/Pa ratios over time without inducing hyperemia in the blood vessel.

2. The method of claim 1, further comprising identifying a dicrotic notch in one or more sets of proximal pressure (Pa) values corresponding to the one or more sets of Pd/Pa ratios; and wherein the step of determining whether the one or more minimum resting Pd/Pa ratios occurs in diastole or systole is based on a location of the one or more minimum resting Pd/Pa ratios relative to the dicrotic notch.

3. The method of claim 1, wherein:
the plot comprises:
   a time varying graph of the plurality of minimum resting Pd/Pa ratios, and
   an indication of an overall minimum resting Pd/Pa ratio.

4. The method of claim 1, wherein:
the plot comprises a discrete point for each of the plurality of minimum resting Pd/Pa ratios.

5. The method of claim 1, wherein:
the step of sampling the sensor further comprises sampling the sensor during a pullback of the intravascular data collection probe through the blood vessel, and
the plot comprises the plurality of minimum resting Pd/Pa ratios that change over time during the pullback.

6. The method of claim 5, further comprising tracking changes in the plurality of minimum resting Pd/Pa ratios along a path of the pullback in the blood vessel to identify a location of stenosis in the blood vessel.

7. The method of claim 6, further comprising displaying a user interface comprising the plot.

8. The method of claim 1, further comprising filtering the one or more sets of Pd/Pa ratios by removing noise or by smoothing a waveform comprising the set of Pd/Pa ratios.

9. A method of assessing a blood vessel of a subject using intravascular data comprising:
sampling a sensor of an intravascular data collection probe disposed in the blood vessel at a sampling rate to obtain a plurality of distal pressure (Pd) values;
receiving, at an intravascular data processing system, the plurality of sampled distal pressure (Pd) values and a plurality of proximal pressure (Pa) values;
determining, using the intravascular data processing system, one or more sets of Pd/Pa ratios based on the plurality of distal pressure (Pd) values and the one or more plurality of proximal pressure (Pa) values, wherein each of the sets of Pd/Pa ratios includes Pd/Pa ratios that are determined through an entirety of one heart cycle;
determining, using the intravascular data processing system, one or more minimum Pd/Pa ratios, wherein each of the one or more minimum Pd/Pa ratios is a minimum among one of the sets of Pd/Pa ratios over the entirety of the corresponding heart cycle;
identifying a dicrotic notch in one or more sets of proximal pressure (Pa) values corresponding to the one or more sets of Pd/Pa ratios;
determining whether the one or more minimum Pd/Pa ratios occur in diastole or systole based on a location of one or more minimum Pd/Pa ratios relative to the dicrotic notch; and
(i) if the one or more minimum resting Pd/Pa ratios occur in systole, inducing hyperemia in the blood vessel, and performing a fractional flow reserve assessment during the hyperemia, or (ii) if the one or more minimum resting Pd/Pa ratios occur in diastole, controlling a display system to generate a plot of the one or more minimum resting Pd/Pa ratios over time without inducing hyperemia in the blood vessel.

10. The method of claim 9, wherein identifying the dicrotic notch in the one or more sets of Pa values is performed by visual inspection.

11. The method of claim 9, wherein identifying the dicrotic notch in the one or more sets of Pa values is performed automatically by the intravascular data processing system.

12. The method of claim 9, wherein:
the step of sampling the sensor further comprises sampling the sensor during a pullback of the intravascular data collection probe through the blood vessel, and
the plot comprises the plurality of minimum resting Pd/Pa ratios that change over time during the pullback.

* * * * *

UNITED STATES PATENT AND TRADEMARK OFFICE
CERTIFICATE OF CORRECTION

| | | |
|---|---|---|
| PATENT NO. | : 11,311,200 B1 | |
| APPLICATION NO. | : 16/186040 | |
| DATED | : April 26, 2022 | |
| INVENTOR(S) | : Gopinath et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 393 days.

Signed and Sealed this
Nineteenth Day of December, 2023

Katherine Kelly Vidal
*Director of the United States Patent and Trademark Office*